United States Patent
Williams

(10) Patent No.: US 6,196,963 B1
(45) Date of Patent: Mar. 6, 2001

(54) BRACHYTHERAPY DEVICE ASSEMBLY AND METHOD OF USE

(75) Inventor: Michael S. Williams, Santa Rosa, CA (US)

(73) Assignee: Medtronic Ave, Inc., Santa Rosa, CA (US)

( * ) Notice: Subject to any disclaimer, the term of this patent is extended or adjusted under 35 U.S.C. 154(b) by 0 days.

(21) Appl. No.: 09/260,344

(22) Filed: Mar. 2, 1999

(51) Int. Cl.[7] .................................................. A61N 5/00
(52) U.S. Cl. ............................................................... 600/3
(58) Field of Search ................................. 600/3, 1, 2, 4, 600/5, 6, 7, 8

(56) References Cited

U.S. PATENT DOCUMENTS

| | | |
|---|---|---|
| 3,324,847 | 6/1967 | Zoumboulis . |
| 3,927,325 | 12/1975 | Hungate et al. . |

(List continued on next page.)

FOREIGN PATENT DOCUMENTS

| | | |
|---|---|---|
| 9110456 | 11/1991 | (DE) . |
| 196 00 669 A1 | 8/1996 | (DE) . |
| 0158630 | 10/1985 | (EP) . |
| 0 182 689 A2 | 5/1986 | (EP) . |
| 0 686 342 A1 | 12/1995 | (EP) . |
| 0813894 | 12/1997 | (EP) . |
| 1308011 | 2/1973 | (GB) . |
| 2 154 761 | 9/1985 | (GB) . |
| WO 95/07732 | 3/1995 | (WO) . |
| WO 96/22121 | 7/1996 | (WO) . |
| WO 97/07740 | 3/1997 | (WO) . |
| WO 98/33555 | 8/1998 | (WO) . |
| WO 99/24116 | 5/1999 | (WO) . |
| WO 99/32192 | 7/1999 | (WO) . |

OTHER PUBLICATIONS

Lindsay, et al., "Aortic Arteriosclerosis in the Dog After Localized Aortic X–Irradiation", *Circulation Research*, Jan. 1962.

Friedman, et al., "The Antitherogenic Effect of Iridium upon the Cholesterol–fed Rabbit", *Journal of Clinical Investigation*, vol. 43, No. 2, 1964.

Friedman, et al., "Effect of Iridium 192 Radiation on Thromboatheroscerotic Plaque in the Rabbit Aorta", *Arch Path*, vol. 80, Sep. 1965.

Hoopes, et al., "Intraoperative Irradiation of the Canine Abdominal Aorta and Vena Cava", *I.J. Radiation Oncology Biology Physics*, vol. 13, No. 5, May 1987.

Weshler, et al., "Inhibition by irradiation of smooth muscle cell proliferation in the de–endothelialized rat aorta", *Frontiers of radiation biology*, Tel Aviv, Oct. 1988.

(List continued on next page.)

*Primary Examiner*—Cary O'Connor
*Assistant Examiner*—Brian Szmal

(57) ABSTRACT

A temporarily implantable brachyherapy assembly is adapted to locally deliver acute doses of radiation to tissue at or adjacent to a body lumen wall. The assembly includes a radiation source which is stored in a housing in radioactive isolation. A first delivery member is adapted to removably engage the radiation source and remove it from storage for delivery to an injured or stenosed region of a vessel. The second delivery member is also a shielding device with a shielded region of substantially radiopaque material, and also with an unshielded region made of substantially radiolucent material and which is distal to the shielded region. A third delivery member or centering device has a lumen through which the second delivery member may be delivered to the treatment site. When not in use or between uses, the radiation source is housed within a storage assembly that includes a radiation shield two opposite windows which are adjustable between open and closed positions.

15 Claims, 11 Drawing Sheets

U.S. PATENT DOCUMENTS

| | | |
|---|---|---|
| 4,359,453 | 11/1982 | Gordon . |
| 4,512,762 | 4/1985 | Spears . |
| 4,625,724 | 12/1986 | Suzuki et al. . |
| 4,646,737 | 3/1987 | Hussein et al. . |
| 4,662,368 | 5/1987 | Hussein et al. . |
| 4,672,962 | 6/1987 | Hershenson . |
| 4,706,652 | 11/1987 | Horowitz . |
| 4,799,479 | 1/1989 | Spears . |
| 4,815,449 | 3/1989 | Horowitz . |
| 4,819,618 | 4/1989 | Liprie . |
| 4,878,492 | 11/1989 | Sinofsky et al. . |
| 4,897,076 * | 1/1990 | Puthawala et al. ............ 600/3 |
| 4,969,863 * | 11/1990 | Van't Hooft et al. ............ 600/3 |
| 5,059,166 | 10/1991 | Fischell et al. . |
| 5,084,001 * | 1/1992 | Van't Hooft et al. ............ 600/3 |
| 5,147,282 | 9/1992 | Kan . |
| 5,199,939 | 4/1993 | Dake et al. . |
| 5,213,561 | 5/1993 | Weinstein et al. . |
| 5,282,781 | 2/1994 | Liprie . |
| 5,302,168 | 4/1994 | Hess . |
| 5,354,257 | 10/1994 | Roubin et al. . |
| 5,411,466 | 5/1995 | Hess . |
| 5,484,384 | 1/1996 | Fearnot . |
| 5,498,227 | 3/1996 | Mawad . |
| 5,503,613 | 4/1996 | Weinberger . |
| 5,540,659 | 7/1996 | Teirstein . |
| 5,607,419 | 3/1997 | Amplatz et al. . |
| 5,611,767 | 3/1997 | Williams . |
| 5,616,114 | 4/1997 | Thornton et al. . |
| 5,618,266 | 4/1997 | Liprie . |
| 5,624,372 | 4/1997 | Liprie . |
| 5,643,171 | 7/1997 | Bradshaw et al. . |
| 5,662,580 | 9/1997 | Bradshaw et al. . |
| 5,683,345 | 11/1997 | Waksman et al. . |
| 5,688,220 | 11/1997 | Verin et al. . |
| 5,707,332 | 1/1998 | Weinbetger . |
| 5,782,742 | 7/1998 | Crocker et al. . |
| 5,840,008 * | 11/1998 | Klein et al. ............ 600/3 |
| B1 5,199,939 | 8/1998 | Dake . |

OTHER PUBLICATIONS

Schwartz, et al., "Effect of External Beam Irradiation on Neointimal Hyperplasia After Experimental Coronary Artery Injury", *JACC*, vol. 19, No. 5, Apr. 1992.

Wiedermann, et al., "Intracoronary Irradiation Markedly Reduces Restenosis After Balloon Angioplasty in a Porcine Model", *JACC*, vol. 23, No. 6, May 1994.

Waksman, et al., "Endovascular Low–Dose Irradiation Inhibits Neointima Formation After Coronary Artery Balloon Injury in Swine", *Circulation*, vol. 91, No. 5, Mar. 1, 1995.

* cited by examiner

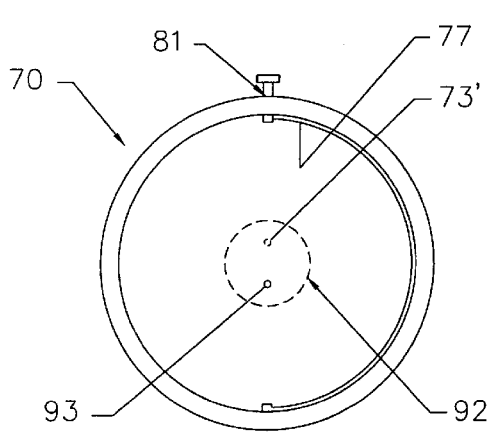
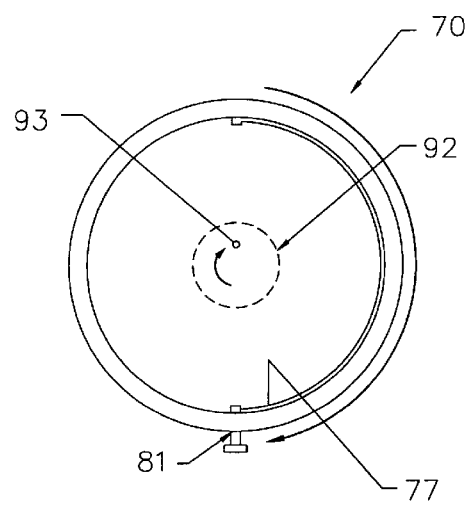
FIG. 6A    FIG. 6B
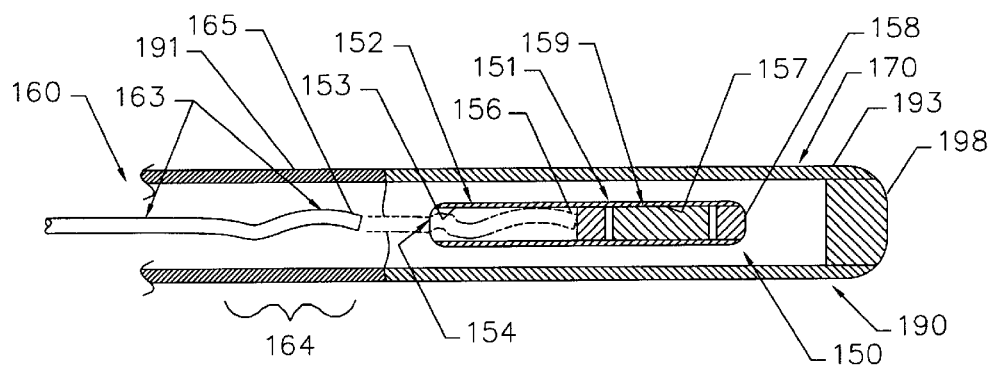
FIG. 7
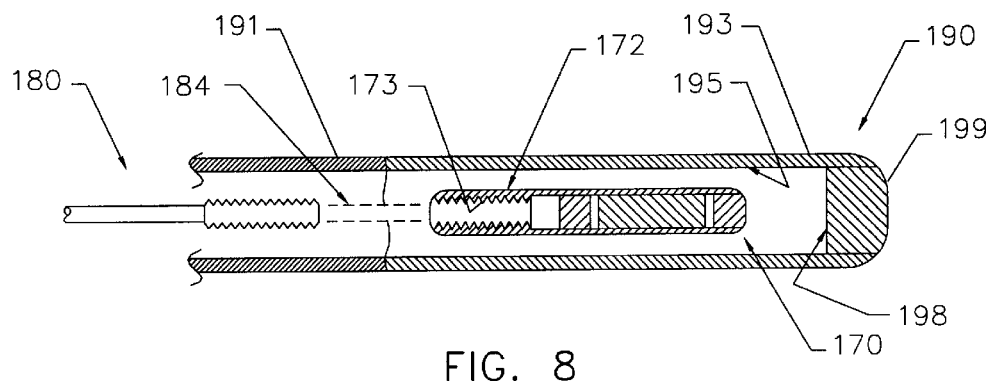
FIG. 8

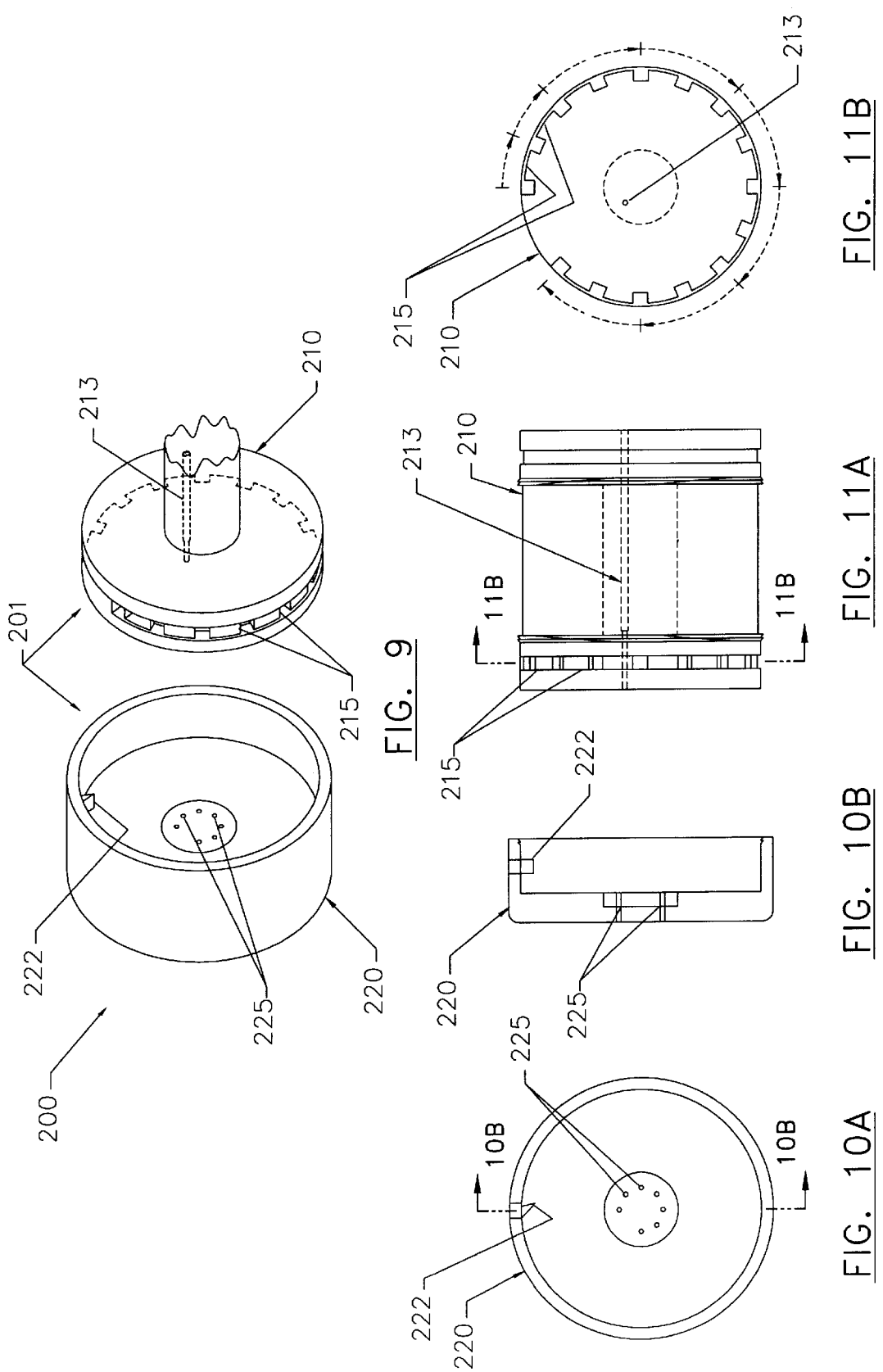

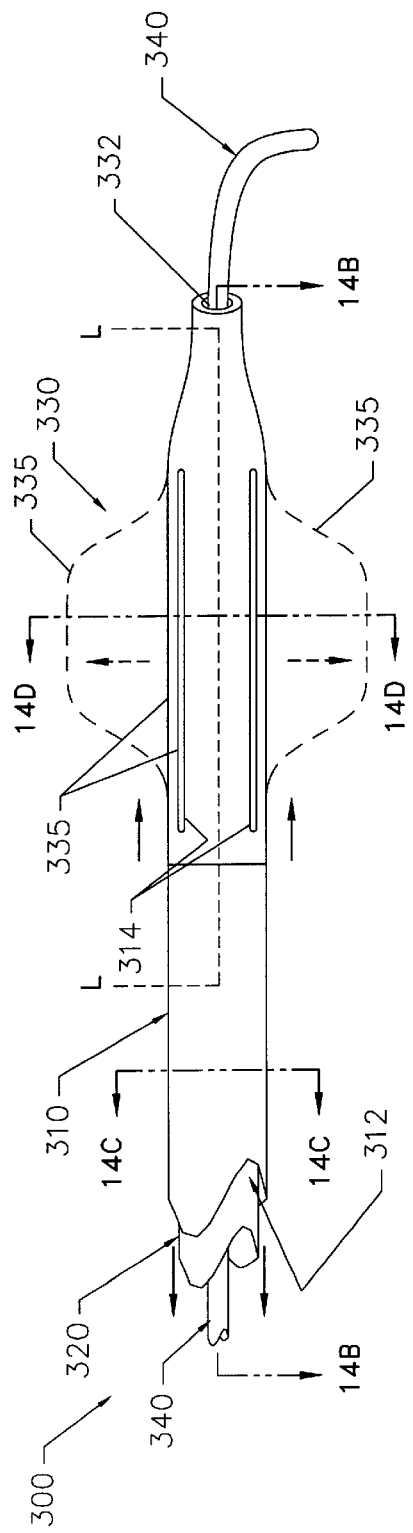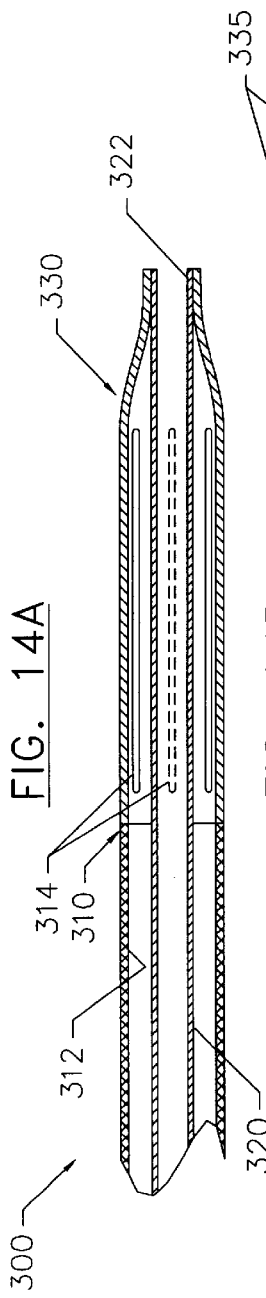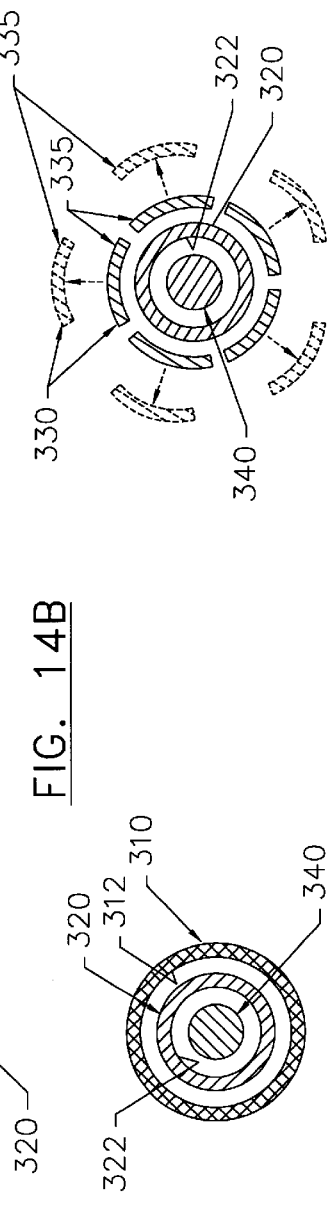

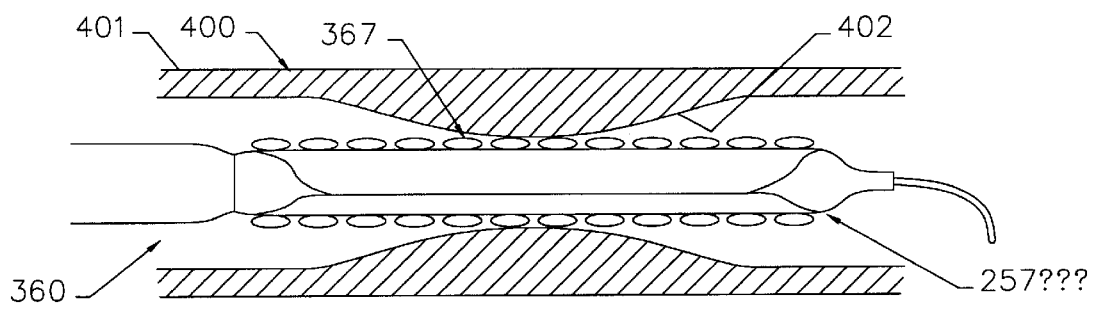
FIG. 16A
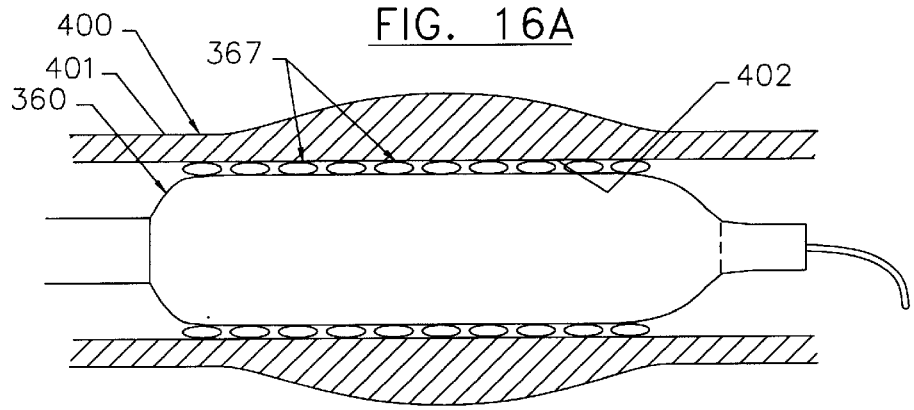
FIG. 16B
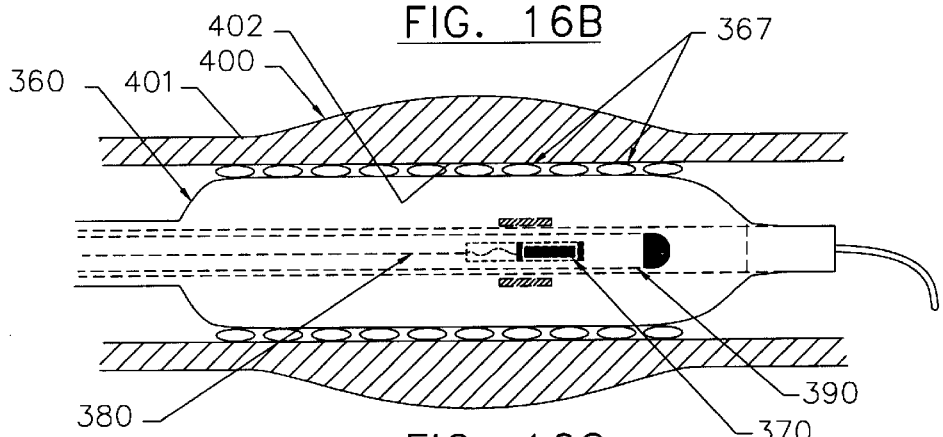
FIG. 16C
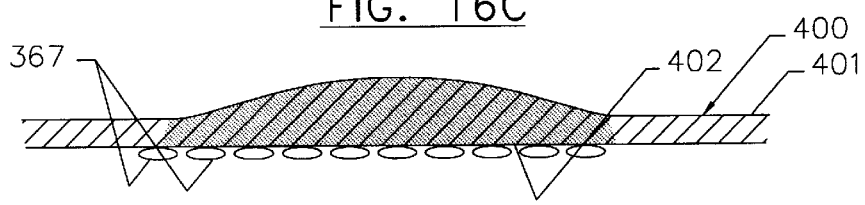
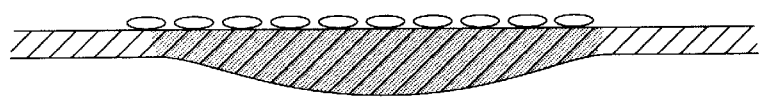
FIG. 16D

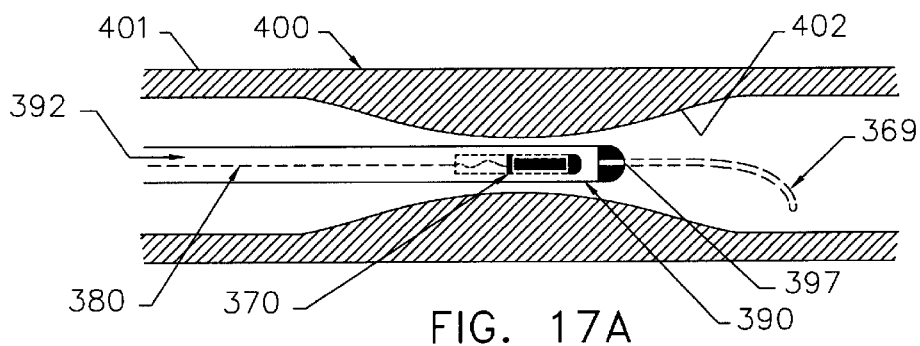
FIG. 17A
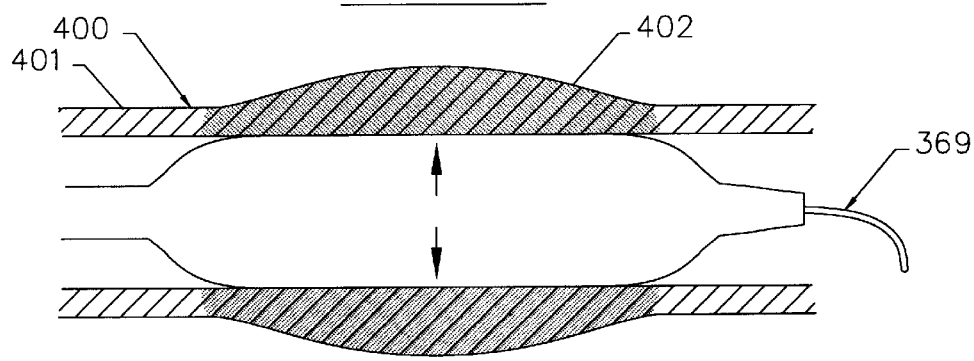
FIG. 17B
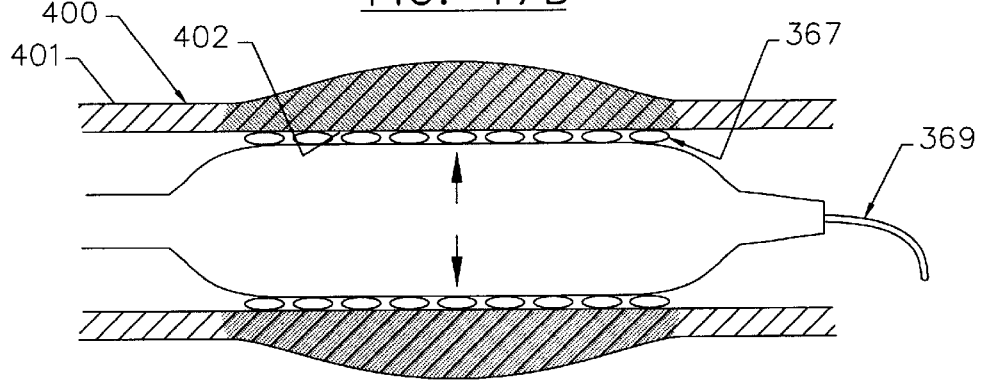
FIG. 17C
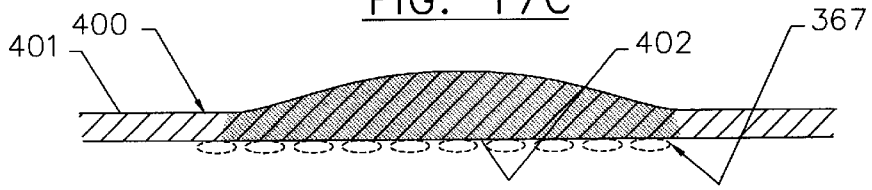
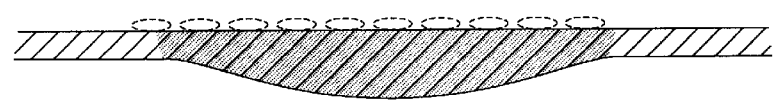
FIG. 17D

BRACHYTHERAPY DEVICE ASSEMBLY AND METHOD OF USE

FIELD OF THE INVENTION

The present invention is a surgical device. Specifically, it is an intravascular brachytherapy system adapted to locally irradiate tissue within a body space. More, specifically, it is a temporarily implantable brachytherapy assembly which is adapted to deliver a radiation source within a vessel lumen for treatment of the vessel wall tissue in order to prevent restenosis ancillary to recanalizing and/or stenting of the vessel.

BACKGROUND

Several medical treatments have been developed which use invasive medical devices for local in situ delivery of energy within body tissues, such as for example in order to treat cancer, or according to other specific examples for preventing or reducing restenosis. Restenosis is an occlusive tissue response to vessel wall injury after recanalization of an occluded region of the vessel, such as through angioplasty, stenting or atherectomy, and has been observed to take place during the first six months after recanalization. Restenosis is believed to be related to an injury response in a vessel wall after balloon expansion of an occlusive lesion, in the case of angioplasty and/or stenting, or during debulking of the lesion site, in the case of atherectomy procedures. This wall injury is further believed to invoke a hyperproliferative response in the smooth muscle cells which make up the vessel wall, such that the proliferating muscle tissue essentially grows into the vessel lumen. This muscle cell proliferation forms at least in part an occlusion at the injury site, minimizing or even reversing the initial result of recanalization. Various localized energy delivery devices which have been disclosed for use in preventing restenosis are generally intended to stunt this hyperproliferative growth of smooth muscle cells in order to substantially reduce the related occlusive response and thereby maintain lumenal patency through the injured site post-recanalization.

According to the known devices which are intended for localized energy delivery to tissue, various specific modes of local energy delivery have been previously disclosed. For example, one known procedure for treating tumors uses a catheter to deliver a ferromagnetic material to a tumor so that the material may heat the tumor when exposed to an ultrahigh radiofrequency electromagnetic field or ultrasonic waves. In another example intended to treat atherosclerosis, microscopic magnetic particles are injected intravenously into a patient, are selectively phagocytized by atherosclerotic cells in a lesion along a blood vessel wall in the patient, and are then heated to therapeutic temperatures by subjecting the magnetized cells to a high frequency alternating magnetic field. Another previously disclosed medical device assembly is adapted to locally emit X-ray radiation into tissue adjacent the catheter. Still further, another known device intended for use in preventing restenosis is adapted to emit ultraviolet light radiation into injured vessel wall tissue. More detailed examples of medical device assemblies and methods which are adapted for local delivery of high levels of energy into tissue, such as of the types just described, are variously disclosed in the following references: U.S. Pat. No. 4,359,453 issued to Gordon; U.S. Pat. No. 5,282,781 issued to Granov et al.; U.S. Pat. No. 5,607,419 issued to Amplatz et al.; and PCT No. WO 97/07740.

Other known devices and related procedures place a radioactive source made of a radioisotope material within a particular body region in order to locally irradiate specific tissue abnormalities within that body region. Such procedures are herein generally referred to interchangeably as "radiation therapy" or "brachytherapy" or "radiotherapy", and include applications which actually treat as well as prevent abnormal conditions in tissue. Medical device assemblies which are adapted for brachytherapy applications are herein interchangeably referred to as tissue "radiation devices" or "brachytherapy devices", or "radiation therapy devices"

Previously disclosed brachytherapy devices include permanent implantable brachytherapy devices, which are adapted for prolonged brachytherapy of tissues, and temporary implantable brachytherapy devices, which are adapted for brachytherapy of tissue. In addition, particular brachytherapy devices have also been disclosed for specialized use in treating specific tissues, including cancer tumors or injured vessel wall tissue for preventive restenosis therapy.

Permanently Implantable Brachytherapy Devices

Known implantable brachytherapy devices which are generally adapted for prolonged brachytherapy of body tissues include, for example, implantable brachytherapy sources for the prolonged treatment of tumors, and implantable brachytherapy stents for the prevention of restenosis.

One previously disclosed implantable brachytherapy device assembly which is intended for use in treating tumors includes a radiation source affixed to a stainless steel wire which is adapted to be delivered through a catheter for implantation within the region of a tumor. The radiation source includes an alloy of Iridium-192 and platinum encased within a pure platinum outer layer.

Another known implantable brachytherapy device assembly which is intended for use in treating tumors includes an implantable radioactive wire that is adapted to be delivered with a delivery wire through a delivery sheath and into the desired body region. Once delivered to the desired region, the implantable wire is detached from the delivery wire and is thereby implanted within that region. The radioactive wire has a level of radioactivity which may be specially selected for a desired procedure, and is particularly disclosed for conjunctive use with excision or chemotherapy, standard therapies in tumor treatment. The radioactive wire is further disclosed to include a radioisotope such as cobalt-60, cesium-137, iridium-192, iodine-125, palladium-103, tantalum-73, tungsten-74, or gold-198. The radioactive wire is also disclosed to include an inner core with an outer buffer layer of high atomic number material, such as a platinum coil, which is adapted to attenuate radiation. The radioactive wire is further disclosed to include a variety of shapes such as a helix in order to adapt the device to the anatomy where implanted and such shapes may further adapt the device for also occluding a space or lumen in the treatment region In addition, the radioactive wire may be further adapted to allow for retrieval from the body tissue by use of a retrieval device.

Several endolumenal prostheses, and more particularly implantable endolumenal stents, have also been disclosed for use as implantable brachytherapy devices. Stents are generally implantable tubular structures which are expandable from a radially collapsed condition, which is adapted for delivery to an implant site, to a radially expanded condition, which is adapted to circumferentially engage a vessel wall at the implant site. Such stents may be expandable either by forcing the stent open, such as by means of an inflatable balloon over which the stent is mounted, or by self-expanding means, such as by elastic recovery to the radially expanded condition after removing the stent from a radially confining sheath or tether. While the stent tubular wall is adapted to mechanically hold a vessel lumen open at the site of wall injury, a through lumen is also provided through the stent to allow for flow through the implant region. It is believed that the mechanical presence of stents in regions of vessel wall injury may reduce restenosis in some patients. Radiation therapy stent devices generally combine the restenosis-preventing benefits that are believed to arise from the mechanical structure of the stent with a brachytherapy means coupled to the stent.

More specifically, previously disclosed radiation therapy stent devices provide a therapeutic dose means either as a coating, in cladding associated with a stent, an additive within the material which makes up the stent wall, by ionic or chemical vapor deposition with subsequent activation as, for example, by neutron bombardment, or otherwise affixed to the stent. The radioactive elements which have been disclosed for use with stent radiation therapy devices are generally adapted to provide therapeutic radioactivity for 4–5 months, and more particular disclosures include the use of Iridium 192, Radon 222, Gold 198, Strontium 90, Radium 192, Iodine 125, and Phosphorus 32 for this purpose.

According to one specific disclosure of a known radiation therapy stent, a Beta emitting radioisotope having a half-life between 1 and 100 days is disclosed to be best suited as a stent coating because of their comparatively short range of action within human tissue, and also because of a comparatively short half-life for the implant. Vanadium 48, having a half-life of 16 days and a scheme where 8% of all decay is accompanied by the emision of a gamma ray, is disclosed as one more detailed radioisotope for use with this radiation therapy stent. In another disclosed variation, phosphorus 32, a 14.3 day half-life beta emitter, is alloyed into steel that is used for the stent wire, and in still a further disclosed variation gold 198 (half-life 2.7 days) is used to coat a spring metal material which forms the stent structure.

More detailed examples of brachytherapy devices which are permanent implants, such as according to the types just described, are variously disclosed in the following references: U.S. Pat. No. 4,819,618 issued to Liprie; U.S. Pat. No. 5,059,166 issued to Fischell et al.; U.S. Pat. No. 5,213,561 issued to Weinstein et al.; U.S. Pat. No. 5,302,168 issued to Hess; U.S. Pat. No. 5,411,466 issued to Hess; U.S. Pat. No. 5,498,227 issued to Mawad; and Published PCT Pat App No. WO 95/07732. The disclosures of these references are herein incorporated in their entirety by reference thereto.

Temporarily Implantable Brachytherapy Devices

Known temporarily implantable brachytherapy devices which provide for acute brachytherapy of tissues generally include an elongate body with a distal end portion that is adapted to be advanced into the desired body space for brachytherapy, and is then removable after the acute dose of radiation is delivered. In more detail, previously disclosed devices of this type are adapted so that the distal end portion may be delivered into the treatment site by manipulating the proximal end portion of the device, such as for example by steering the distal end portion of the device as a guidewire by torquing and advancing the device's proximal end portion, or by slidably engaging and tracking over a guidewire positioned within the body space by means of a lumen extending through the brachytherapy device, or by simply advancing the delivery device as a probe through the lumen of another delivery catheter. Such devices are generally intended for use in treating tissue at or adjacent to a lumenal or body space wall, although at least one known temporarily implantable brachytherapy device is intended for use within a blood vessel but for the primary purpose of irradiating blood flowing through the vessel and around the device without irradiating surrounding body tissues. More detailed examples of devices of this type are disclosed in U.S. Pat. No. 3,927,325 issued to Hungate et al.

Other more specific types of temporarily implantable brachytherapy devices which have been previously disclosed include radiation sources that are adapted to locally deliver radiation to tissue by: directly coupling the source to an expandable member which is adapted to position the source at or immediately adjacent to a lumen wall during brachytherapy treatment; fixedly engaging the source to a catheter centrally within an expandable member on the catheter; and coupling the source to a wire or probe that is not fixedly coupled in relation to a centering member, although including combination assemblies of such wires or probes with separate delivery catheters which may have centering members.

Known temporarily implantable brachytherapy devices which directly couple a radiation source to an expandable member generally use the expandable member to place the source in direct contact with or closely adjacent to a lumen wall. According to this arrangement, such devices are generally intended to emit radiation energy into the wall tissue at closer range, and therefore, at higher dose per unit time than if the source were not directly coupled to the tissue as such.

One example of a known device of this type directly couples a radiation source to lumenal wall tissue by use of an expandable balloon and is intended for use in restenosis prevention. The device includes a series of radioactive elements, which may include Radon 222, Gold 198, Strontium 90, Radium 192, and Iodine 125, and which are positioned in a circumferentially and longitudinally spaced arrangement on the skin of an expandable balloon positioned at the distal end of a balloon catheter.

Another known temporarily implantable device and method directly inflates a balloon with a radioactive fluid. In one disclosed example, an angioplasty balloon is inflated with a material suspension of a beta emitting material such as Iodine 125 or Phosphorus 32. The balloon may be filled with the radioactive suspension either during or after angioplasty, and is adapted to emit the radiation from the treatment balloon surface. Further disclosed embodiments provide additional balloons on the catheter assembly as safeguards against the dangerous potential for the radioactive inflation suspension to leak from the balloon and into the body, such as in the case of a balloon rupture. In still a further disclosed variation, a shielded injector or pump is permanently affixed to the catheter shaft in order to prevent spillage of the harmful radioactive fluid during use.

Still another device assembly and method for preventing restenosis couples a radiation source to spring wires which form an expandable wire basket. The wire basket is expandable to engage the desired body tissue when advanced distally from an outer, radially confining sheath which is constructed of polytetrafluoroethylene. In one disclosed variation, an alloy of iridium with stainless steel forms the spring wires which are themselves the radioactive source. Further disclosed variations include: coating the spring wires with a radioactive surface coating, such as iridium particles imbedded in polymer; plating radioactive iridium onto the spring wires; or disposing a plurality of radioactive iridium tubular sleeves around the spring wires. According to further disclosure of the overall assembly, the catheter when the expandable cage is retracted in the sheath is 8 French (2.7 millimeters or 0.105 inches) in diameter, and the expandable portion is approximately 7 millimeters long and 3 millimeters in diameter when fully expanded, although may range from 0.5 to 4.0 millimeters in diameter.

Other more detailed examples of temporarily implantable brachytherapy devices which directly couple a radioactive source to an expandable members in order to directly engage the target tissue with the source are variously disclosed in the following references: U.S. Pat. No. 5,411,466 issued to Hess; U.S. Pat. No. 5,302,168 issued to Hess; U.S. Pat. No. 5,616,114 issued to Thornton et al.; U.S. Pat. No. 5,662,580 issued to Bradshaw et al.; and U.S. Pat. No. 5,484,384 issued to Fearnot.

Other known brachytherapy devices provide a radiation source fixedly attached to a delivery catheter centrally of a centering member in order to center the radiation source within the lumen when the expandable member expands to engage the lumenal wall. According to these previous disclosures, the radiation source is generally intended to be positioned equidistant from all points along the lumen's circumference which is engaged to the centering member and surrounds the source It is believed, according to the prior disclosures, that the centering of the radiation source in this manner may allow for a more uniform delivery of therapeutic radiation about the lumen's circumference, which is further believed to provide a safer, more repeatable and predictable brachytherapy treatment of the lumen wall tissue.

One example of such a known temporarily implantable brachytherapy device is intended to allow for brachytherapy post-angioplasty without separately inserting a radiation source and includes a catheter with particles or crystals of radioactive material, such as Cobalt-60, imbedded onto a tubular member extending beneath an angioplasty balloon. A retractable radiation shielding sleeve is slidable along the tube beneath the balloon and selectively covers the source material, blocking exposure to radiation until the shield is shifted away. After completion of angioplasty with the expandable balloon, the shielding sleeve is retracted and the area of the injury is irradiated.

Another known temporarily implantable tissue brachytherapy device assembly includes discrete radioactive treating elements engaged to an inner tube extending within an angioplasty balloon and is intended to irradiate a stenotic site simultaneously instead of sequentially with balloon angioplasty. The treating elements are ring-shaped or donut-shaped and are positioned either between the balloon membrane and an inner tube or between coaxial tubular walls of the catheter which are located within the balloon. Stop rings, preferably of radiopaque material, are positioned at each end of the string of treatment elements to maintain the string at a fixed location within the balloon and to aid in locating the catheter at a desired location. The treatment elements are disclosed to generally include any alpha, beta, or gamma particle emitting substance, although preferably is a pure beta-particle emitter, or beta and gamma emitter. More detailed examples of radiation emitting substances which are disclosed for use in this assembly include Strontium-90, Ruthenium-106, Phosphorus-32, Iridium-192, and/or Iodine-125. It is further disclosed that the amount and strength of the radioactive material contained in the combined number of treating elements should be sufficient to deliver a desired dosage of from 100 to about 10,000 rads, preferably about 700 to 5,000 rads, in about 2 to 10 minutes. The level of radioactivity for the elements to deliver the preferred dosage may be up to 25,000 mCi per centimeter of vessel to be treated, depending upon the radiation source used.

Other more detailed examples of temporarily implantable brachytherapy devices which provide radiation sources fixedly located on catheter members centrally within expandable members as centering devices, such as according to the types just described, are disclosed in the following references: U.S. Pat. No. 5,213,561 issued to Weinstein et al.; and U.S. Pat. No. 5,683,345 issued to Waksman et al. The disclosures of these references are herein incorporated in their entirety by reference thereto.

Other disclosed temporarily implantable brachytherapy devices which couple a radiation source to a wire or probe include: brachytherapy guidewires, such as a wire having a distal end portion with a radiation source that is adapted to be steered into a body space by torquing and advancing the wire's proximal end portion externally of the patient; and brachytherapy wires or probes which are adapted to be delivered into a desired body space through separate delivery sheaths or catheter assemblies, including probes with a radiation source fixedly positioned within the probe's distal end portion, or probes which are adapted with a lumen to receive a radiation source having a separate delivery means within the probe's distal end portion.

One known temporarily implantable brachytherapy device of this type which is intended for use in preventing restenosis includes a radiation means engaged within a lumen extending within an elongated carrier with three regions of distally increasing flexibility. The radiation means is positioned within the distal, flexible portion of the carrier, and in one variation includes a plurality of spaced iridium pellets frictionally engaged within the lumen. In one disclosed variation, a radioactive liquid, powder, or gas may be either fixed in place in the distal section of the carrier before placement in a lumen, or may be injected into the distal section after placement. The device is used by placing a guidewire within the vasculature, advancing an introducing catheter over the guidewire, and inserting the radioactive device into the introducer catheter such that the radioactive segment extends beyond the end of the probing catheter and adjacent to the selected portion of vessel wall tissue to be irradiated. The disclosed level of total radiation to be provided is from 100 to about 10,000, preferably from about 500 to about 5,000, and typically about 3000 rads per hour along the length of the radioactive segment as measured at 3 millimeters from the longitudinal central axis of the carrier. The radioactivity of the radioactive pellets which is believed necessary to achieve this result is further disclosed to be from 0.01 to about 100,000 millicuries, preferably from about 50 to 500, and typically about 100 millicuries per centimeter of length of radioactive pellets.

Another example of a known brachytherapy device assembly which is also intended for use in preventing restenosis includes a brachytherapy device with a distal end with a tip and wire wound housing that contains a radioactive dose means and that has a window cut-out for exposing the radiation dose means. A wire wound retractable sheath is positionable over the radioactive dose means and is retractable to expose the window cut-out portion of the housing such that the dose means may be exposed to a lesion site. The radiation dose means is disclosed to include a radioactive material which may be Radon 222, Gold 198, Strontium 90, Radium 192, and Iodine 125, and may be further provided in a solid, liquid, or gaseous form.

Another known brachytherapy device which is intended for use in treating tumors includes a source wire with a continuous stainless steel tube which encases a backbone wire and a cylindrical radioactive core further enclosed within the tube by way of a plug at the tube's distal end. The radioactive core is made of a pure iridium rod which is, prior to final assembly within the source wire, irradiated within a nuclear reactor to form Iridium 192 having level of radioactivity sufficient to treat tumors. A robotic laboratory unit within a radiation shielded room is used for final assembly of the "hot core" within the source wire. In one disclosed "high radioactive dose source wire" variation, the tube has an outer diameter of 0.023 inches and the core has a 0.843 mm outer diameter, a 10 millimeters length, and a level of radiation from 1 to 10 curies. Another disclosed "high-dose" source wire variation has an outer diameter of 0.018 inches and includes a two centimeter long, 21 milligram core irradiated to 10 curies. In one disclosed application, the "high dose" source wire is delivered through a 10-French catheter, and in a preferred mode also through a protective closed-end sheath of standard biocompatible material which is positioned adjacent a pancreatic cancer tumor along the gastro-intestinal tract. In another disclosed "low dose, mini-dose" source wire variation, the tube has an outer diameter of 0.020 inches, the core has a 0.005 inch outer diameter and is irradiated from 200 to 500 millicuries, and the source wire is delivered to a tumor through a 21 gauge needle. A radiation shielded, automated loader is used to load or retrieve the source wire into or from the respective delivery device during use.

Yet another known brachytherapy device which is intended to prevent restenosis includes a guidewire with a radiation source made of a tubular iridium sleeve which may be positioned: over a tapered core wire and beneath a distal coil; over a safety wire, which is secured to a core wire, and beneath a distal coil; or over a core and between proximal and distal coils. A further disclosed variation includes a plastic tubular catheter with a tubular iridium sleeve that is fixedly embedded in the distal portion of the elongated catheter which also includes a passageway adapted to track over a guidewire to a treatment site. The catheter is disclosed to have an outer diameter of 0.038 inches and is insertable into a desired treatment site through a guiding catheter.

More detailed examples of the temporarily implantable brachytherapy devices which couple a radiation source to a probe or wire to be delivered to a desired site, such as of the types just described, are variously disclosed in the following references: U.S. Pat. No. 5,282,781 issued to Liprie; and U.S. Pat. No. 5,624,372 issued to Liprie; U.S. Pat. No. 5,199,939 issued to Dake et al.; U.S. Pat. No. 5,213,561 issued to Weinstein et al.; U.S. Pat. No. 5,302,168 issued to Hess; U.S. Pat. No. 5,354,257 issued to Roubin et al. The disclosures of these references are herein incorporated in their entirety by reference thereto.

In addition to the brachytherapy devices of the types just described above, other known brachytherapy treatment device assemblies and methods provide a brachytherapy device in combination with a centering member provided on a separate delivery catheter. The general purpose of such a combination assembly is to position the radiation source centrally within a lumen, such as described previously above for other assemblies having the source fixed on a catheter centrally within the centering member. The combination assemblies of the present type, however, are generally intended to allow for controlled delivery of the radiation source delivery separately of the centering catheter. In addition, it is believed that the structure, material, and design of the radiation source may be more beneficially adapted for a particular treatment according to this combination design.

One example of a known brachytherapy device assembly of this combination type positions a radiation source within a balloon by using fluid to force the source along a lumen extending along the centering catheter and beneath the balloon. The balloon catheter according to this assembly includes a pair of adjacent parallel inner tubes, one forming a guidewire lumen and the other a treating element lumen. The two lumens are contained within an outer tube and the space between the outer tube and the inner tubes forms a fluid return lumen and may also be used to inflate the balloon. Pressurized blood compatible fluid such as sterile saline is used to advance treating elements along the treating element lumen while simultaneously inflating the balloon. Accordingly, angioplasty is performed at the same time that the treatment elements are advanced into the balloon region for brachytherapy treatment. The treating elements may be retrieved by reversing the flow through the return and treating element lumens.

Another known combination brachytherapy device which is intended for the prevention of restenosis provides a radiation dose delivery wire in combination with a balloon catheter. The balloon catheter includes a guidewire lumen which is adapted to track over a guidewire to the desired treatment site, an inflation lumen for expanding the balloon, and a blind lumen adjacent to the guidewire tracking lumen that is closed distally of the balloon and which is adapted to receive the radiation source wire. The radiation source wire is disclosed to include a non-radioactive section and a radioactive section which encapsulates a radioactive source including one or more pellets of Iridium 192, Iodine 125, or Palladium 103, wherein a single pellet may have a radioactivity of less than or equal to 10 Curies, and wherein the radioactive section may be from 2 to 10 centimeters long. According to the disclosed use for this assembly, the balloon catheter is tracked over the guidewire to the treatment site. The radiation dose delivery wire is then advanced within the blind lumen until the radioactive source is substantially adjacent the target area for brachytherapy treatment. The time which the radioactive source is to remain adjacent to the treatment site depends upon the activity of the source, the diameter of the artery at the target area, and the desired dosage to be delivered. A radiation shield may be used during use and is a large apparatus on rollers which is positionable between a patient and an operator of the assembly.

The assembly just described is further disclosed for use with a computer controlled afterloader which allows an operator to input variables for activity of the radioactive sources, the date delivered to the target area, the diameter of the artery at the target area, the length of the target area, and the value of the desired dose to be delivered. The computer controlled afterloader then calculates the time the source must be adjacent to the target, moves the radiation dose delivery wire toward the desired location within the balloon catheter, waits the calculated time (and may oscillate the radiation source wire a given distance back and forth within the balloon region during this time), and then pulls the radiation dose wire back out of the balloon catheter The computer controller may also be programmable and may further include a database memory for storing the number of times that a particular radioactive source has been used.

Another known brachytherapy device assembly which is intended for the prevention of restenosis includes a catheter with a centering member which may be a balloon or wires or loops and which is designed for the purpose of delivering an irradiation ribbon to a desired treatment site. The catheter includes a lumen with a closed end that is adapted to receive an irradiation ribbon to be positioned substantially centrally within the centering member. Disclosed variations for the centering member include: an inflatable balloon formed as a coil around the catheter's outer surface, a plurality of essentially annular balloons, a plurality of flexible wire loops which may be self-expanding when released from a withdrawable retaining sheath or expandable by a longitudinally movable expansion means. Further disclosed variations of the wire expansion means embodiment include: advancing free ends of the wires toward the distal extremity of the device where the wires are secured, or pulling on the wires having loops with distally located free ends. In addition, further disclosed variations also provide for the balloon or wire loops to have a geometry adapted to bias the positioning of the lumen including the radioactive material closer to one side of the blood vessel. Still further, a bent guidewire may be used to bias the catheter body to have a desired radial orientation within a treatment location according to a physician's desire.

Another known brachytherapy device assembly which is also intended for use in preventing restenosis provides a balloon catheter with a lumen that is adapted to track over a guidewire to a desired treatment site, but which includes a filter that is positioned within the lumen and which does not allow a radioactive source wire to pass distally from the lumen. The balloon catheter first tracks over a guidewire engaged within the lumen to the desired site. Then the guidewire is removed and replaced with the radiation treatment wire that advances beneath the balloon and until confronting the filter The filter may be constructed according to various disclosed variations, including for example one or more membranes that are penetrable by the guidewire but not by the source wire, a one-way valve such as a flap, or a simple constriction within the lumen's inner diameter that is large enough to allow the guidewire to pass but not sufficiently large to pass the radiation source wire.

The disclosed construction of the catheter according to the assembly just described includes a hollow, generally cylindrical member constructed of a flexible member such as polyethylene glycol with an interior made of or coated of a friction reducing material, such as TEFLON, to aid in passing the guide wire and radioactive sources. Various balloon variations are also disclosed according to this assembly and include: an inflated geometry which is ribbed or pleated in a symmetrical pattern to center the inner lumen with the radiation source as well as to allow blood flow to perfuse between the pleats or ribs; and soft, flexible, raised portions on the outer surface of an otherwise symmetrical balloon which serve as spacers from a lumen wall for perfusion. Another disclosed centering catheter embodiment replaces the expandable balloon with a plurality of strategically placed bumps or feelers on the external surface of the catheter, which bumps or feelers may be constructed of soft material such as Teflon, silicon, polyethylene glycol, etc. The radiation source wire is further disclosed to include gamma type radiation sources such as cesium 137, cobalt 60, iodine 125, iodine 131, cobalt 57, iridium 192, gold 198, and palladium 103.

A further example of a device assembly which combines a brachytherapy device with a separate centering catheter includes a radioguide catheter with a treatment channel through which a radiation source may be advanced. The radioguide catheter includes a centering means for centering the treatment channel within the lumen and which is adapted to allow for blood perfusion during centering and may further be a molded catheter tip, a wire form or a balloon. Disclosed variations of the balloon mode for the radioguide catheter include balloons having helical lobes, straight flutes, or other features on the exterior surface which define a corresponding passageway between the balloon and vessel wall for blood perfusion during inflation. Furthermore, the centering member may alternatively be eccentric to offset an eccentric location of the treatment channel within the radioguide shaft for some particular disclosed variations. One or more longitudinal holes may also be provided on the radioguide catheter for passage of a guidewire and for balloon inflation. This assembly is further disclosed for use with an afterloader which is adapted to automatically step or gradually move the distal tip of a source wire along the balloon region of the radioguide.

The radiation source wire which is disclosed for use in combination with this radioguide catheter just described includes a flexible elongate member with a radiation source assembled at the distal tip which may be pushed through the treatment channel in the radioguide until the source is disposed at the target area and centered there with the centering means. The preferred dose range which is disclosed according to the use of this assembly for treating restenosis is 1,500 to 2,500 rads. In one particular disclosed example for using this assembly, an Iridium 192 source is used to deliver 1,900 rads within a 3 millimeter diameter artery, and may be centered with a 0.5 millimeter tolerance within that artery to deliver therapeutic doses at the closest and furthest radial points along the vessel wall. Other examples using Beta emitters for the radiation source are disclosed to require more precise centering than the Iridium 192 example.

Another known brachytherapy device for use in restenosis prevention includes a catheter with a balloon for insertion into a desired body lumen for treatment, a radioactive radiation means, and a manipulation means or guidewire with a distal end adapted to couple with the radioactive radiation means in detachable interlocking engagement and to advance and remove the radioactive radiation means into and from the catheter. When not in use, the radioactive radiation means is supported within a shielding applicator having a base box with a single lumen extending therethrough. One end of the box has a cover with a first removable plug which closes the lumen at that end, and the other end of the box is tapered and includes a second removable plug closing the lumen at that end. The radioactive radiation means is contained within the lumen between the opposite plugs in an orientation adapted to detachably interlock with the manipulation means. The first plug may be removed to allow the distal end of the manipulation means to be advanced within the lumen to interlockingly engage the radioactive radiation means. Removal of the second plug allows the tapered end to be inserted into a conventional luer connector on the proximal end of a balloon catheter located in the body vessel and having a lumen extending therethrough. The guidewire and radioactive radiation means are advanced through the luer connector and along the balloon cacheter's lumen into the body space for treatment.

One variation for the radioactive radiation means of this assembly includes a bar of radioactive Yttrium 90 in a cover of neutral Titanium material. An upwardly curved elastic arm extends from the covered Yttrium bar and terminates by a stone forming a recess that is intended to engage with a circularly shaped recess formed by another stone at the end of the manipulation guidewire means. The shielding applicator includes a flared entry at the covered end of its lumen which allows the radioactive radiation means to be stored with the arm curved upwardly. By advancing the manipulation means against the radioactive radiation means within the lumen and away from the flared entry, the arm is urged toward the guidewire such that the stone on the guidewire is interlocked with the stone of the radioactive radiation means The guidewire and radioactive radiation means remain engaged in this arrangement while advancing the assembly along the lumen of the balloon catheter and until the coupled assembly is again withdrawn to the location of the flared entry where the arm again biases upwardly from the guidewire and detaches.

Another variation of this brachytherapy assembly includes a radioactive radiation means with a bar of Yttrium 90 covered with Titanium, such as according to the specific variation just previously described, but includes a straight rigid arm terminating in a stone that defines a recess. The stone and recess of this arm are adapted to interlockingly engage a recess formed by another cylindrical or cubical stone on the distal end of the manipulation means guidewire when the guidewire and radiation means are advanced within the lumen of the shielded applicator and balloon catheter.

Still another variation of this brachytherapy assembly includes a radioactive radiation means which is a simple bar of the radioactive Yttrium 90 covered with Titanium, similar to the other embodiments just described. This radioactive bar is housed within a recess, located on a lower box portion which is adjacent the lumen through the shielding applicator, when the shielding applicator is turned in one orientation. The manipulating means is advanced within the lumen of the shielding applicator, a recess on the manipulating means is positioned to face the radiation means, the shielding applicator is then inverted so that the radiation means falls into the manipulating means recess, and the manipulating means is then advanced within the lumen beyond the shielding applicator recess and within the balloon catheter lumen as previously described.

Another disclosed variation for the radioactive radiation means of the brachytherapy assembly just described includes a coiled filament of radioactive material such as Yttrium 90 that is coated with a neutral material of Titanium. A larger pitched coiled filament extends from the radioactive filament and is oriented toward the covered end of the shielding applicator. The distal end of the guidewire has a threaded end which pushes the larger pitched end of the coil until the radioactive coil confronts the opposite plug closing the lumen. The threaded guidewire end is then screwed into the larger pitched coil which is disclosed to be held in place by friction within the lumen, after which the plug is removed and the coupled assembly is engaged to a balloon catheter as described above.

Further more detailed examples of temporarily implantable brachytherapy device assemblies which deliver a brachytherapy device to a treatment site within a centering member on a separate delivery catheter assembly, such as according to the types just described, are variously disclosed in the following references: U.S. Pat. No. 5,411,466 issued to Hess; U.S. Pat. No. 5,503,613 issued to Weinberger; U.S. Pat. No. 5,540,659 issued to Teirstein; U.S. Pat. No. 5,618,266 issued to Liprie; U.S. Pat. No. 5,643,171 issued to Bradshaw; U.S. Pat. No. 5,683,345 issued to Waksman et al.; U.S. Pat. No. 5,688,220 issued to Verin et al.; and European Patent App No. 0 686 342 A1.

There is still a need for a temporarily implantable tissue brachytherapy device assembly that includes a radiation source on a first delivery member which engages and delivers the radiation source to the desired site through a separate delivery catheter assembly which shields tissue proximally of the desired site from the radiation source while allowing radiation from the source to emit from the source and through the delivery catheter assembly once positioned at the desired site.

There is also still a need for such a temporarily implantable tissue brachytherapy device assembly wherein the delivery catheter assembly also provides a centering member which is further adapted to controllably position the radiation source substantially at the radial center of the body space at the treatment site in order to irradiate the tissue evenly and at known radiation levels along the circumference of the body space wall surrounding the radiation source at the treatment site.

There is also still a need for a temporarily implantable tissue brachytherapy device assembly which includes a radiation member with a radiation source and which also includes a delivery member that is adapted to removably engage the radiation member for subsequent delivery into a desired treatment site simply by pushing the delivery member against the radiation member while the radiation member is confined within a storage chamber, such as by way of a spring on the delivery member which is compressible against an outward bias force when advanced against a source coupler and within a source passageway provided by the radiation member.

There is also still a need for a temporarily implantable tissue brachytherapy device assembly that includes a storage assembly with a housing and a storage chamber for storing a radioactive source in substantial radioactive isolation, and which includes a window engaged to the housing and coupled to the storage chamber and that is adjustable to open the storage chamber and allow the source to be engaged with and removed by a delivery member for subsequent use in tissue brachytherapy treatment.

There is also still a need for a temporarily implantable tissue brachytherapy device assembly with a storage assembly that stores several radiation sources in separate storage chambers, such that a particular source may be chosen from the several as appropriate for a particular tissue brachytherapy procedure, and further such that the particular chosen source may be selectively engaged to a delivery device and removed from the storage assembly for subsequent brachytherapy use.

There is also still a need for a temporarily implantable tissue brachytherapy device assembly with a reuseable radiation member stored within a storage chamber which is adapted to control the number of times the radiation member may be reused.

There is also still a need for a temporarily implantable tissue brachytherapy device assembly that includes a storage assembly which is adapted to store a radiation source, including one or more individual radiation members, in substantial radioactive isolation and which is further adapted to allow a radiation member of the radiation source to be removably engaged with and removed by a delivery member for brachytherapy use, and that further includes a monitor coupled to the storage assembly which is adapted to monitor the value of a predetermined parameter of the radiation source.

SUMMARY OF THE INVENTION

The present invention is a temporarily implantable tissue brachytherapy device assembly which is adapted to deliver radiation to a region of tissue at a desired location along a body space wall of a body space in a patient. The invention provides the localized radiation delivery with a radiation source which is engaged to the distal end of a first delivery member and which is adapted to be positioned at the desired region within the body space by manipulating the first delivery member's proximal end portion outside of the patient's body.

One mode of the invention includes a delivery catheter assembly which is adapted to deliver the first delivery member and engaged radiation member to the desired location within the body space. The delivery catheter assembly includes a proximal radiation shield, a distal unshielded body extending distally from the proximal radiation shield, and a radiation passageway which extends between a proximal port along the proximal radiation shield and the distal unshielded body. The distal unshielded body is adapted to be positioned within the body space at the desired location by manipulating the proximal radiation shield externally of the patient. The first delivery member is adapted to slideably engage the radiation passageway through the proximal port such that the radiation member is positioned within the radiation passageway along distal unshielded body. Further to this mode, the proximal radiation shield is further adapted to substantially prevent radiation from transmitting radially, or axially from the radiation member within the radiation passageway, and the distal unshielded body is further adapted to allow such radiation to transmit from the radiation member radially into tissue at the desired location. Accordingly, the tissue proximally of the desired treatment location is shielded from radiation during delivery of the radiation member to the treatment site. It is further noted, however, that the proximal section of the delivery catheter need not necessarily be shielded.

In one aspect of this mode, the delivery catheter assembly further includes a centering member along the distal unshielded body. The radiation passageway according to this aspect terminates distally of the centering member, and the centering member is adapted to position the radiation passageway substantially at the radial center of the body space at the desired location. This combination assembly is thus adapted to uniformly irradiate all regions of tissue along the lumenal circumference at the desired treatment site, in addition to doing so without irradiating tissue proximally or distally of that site.

In one further variation of this aspect, the delivery catheter assembly includes a second delivery member and a separate centering device. The second delivery member includes a delivery passageway extending between a proximal shielded portion and a distal unshielded portion. The centering device includes a centering passageway extending between its proximal end portion and a distal location distally of a centering member on its distal end portion. The second delivery member is adapted to slideably engage and advance along the centering passageway until the unshielded portion is positioned within the centering member. The first delivery member is further adapted to slideably engage and advance along the delivery passageway until the radiation member is positioned within the distal unshielded portion and also within the centering member. According to this variation, the proximal radiation shield of the delivery catheter assembly is therefore formed by the proximal shielded portion of the second delivery member and a proximal end portion of the centering device. Furthermore, the distal unshielded body of the delivery catheter assembly is formed by the distal unshielded portion of the second delivery member and the distal end portion or centering region of the centering device.

According to one detailed embodiment for the second delivery member of this delivery catheter assembly variation, the proximal shielded portion is constructed of a radiation non-transmissive material. In another second delivery member embodiment the distal unshielded portion is constructed of a radiation transmissive material. The terms "substantially radiation non-transmissive" and "substantially radiopaque" are used interchangeably herein, as are the terms "substantially radiation non-transmissive" and "substantially radiolucent".

In another detailed embodiment for the centering device of this variation, the centering device is adapted to track over a guidewire to the desired treatment site in the body space as a third delivery member. In still a more particular embodiment, the centering lumen in particular is adapted to slideably engage and track over a guidewire. In another embodiment, the centering member is an expandable member and is adjustable from a radially collapsed condition, which is adapted to be delivered into the body space, to a radially expanded condition, which is adapted to radially engage the body space wall. Further to this embodiment, the expandable member may be an angioplasty balloon such that tissue brachytherapy may be performed by positioning the radiation member within the radiation passageway beneath the balloon either before, during, or after inflating the balloon to dilate a lesion in an angioplasty procedure.

According to still another detailed embodiment of this delivery catheter assembly variation, the delivery passageway is closed along the distal end portion of the second delivery member. In still a more particular embodiment, the delivery lumen is closed with a shielded plug made of a radiation non-transmissive material in order to shield tissue or fluids distally of the delivery passageway from radiation emitting from the radiation member positioned within that lumen.

Another mode of the invention is a temporarily implantable tissue radiotherapy device assembly with a radiation member adapted to removably engage a delivery member, and provides the radiation member with a source coupler with an inner surface that forms a source passageway, and further provides the delivery member with a delivery coupler that includes a spring. The spring is adapted to engage the source passageway of the source coupler such that an outward bias force from the spring is directed against the inner surface to thereby hold the radiation member and delivery member in interlocking engagement. According to this combination assembly, the radiation member and delivery member may be removably engaged simply by pushing the delivery member against the radiation member such that the spring compresses within the source passageway of the source coupler.

In one aspect of this detachably engaged radiation member-delivery member mode, the delivery member includes a core member and the spring is integrally formed from that core member. In one further variation, the spring is formed as a shaped region of the core and is compressible within the source coupler simply by pushing the shaped region within the source passageway.

Another mode of the invention is a temporarily implantable brachytherapy device assembly that includes a radiation member engaged to the distal end of a delivery member, a delivery catheter assembly with an expandable centering member on its distal end portion, and an endolumenal prosthesis coupled to an outer surface of the expandable centering member. A radiation passageway, which is adapted to slideably receive the first delivery member and radiation member, extends between a proximal port along the delivery catheter assembly's proximal end portion and the delivery catheter assembly's distal end portion distally of the centering member. The centering member is an expandable member and is adjustable from a radially collapsed position, which is adapted to be delivered into the body space, to a radially expanded position, which is adapted to radially engage the body space wall at the desired location such that the centering lumen is positioned substantially at the radial center of the body space at the desired location. The endolumenal prosthesis may be an implantable stent and is adjustable with the expandable member from a radially collapsed condition, which is characterized by the expandable member in the radially collapsed position, to a radially expanded condition, which is characterized by the expandable member in the radially expanded position and is adapted to circumferentially engage the body lumen wall at the desired location.

According to this mode, tissue brachytherapy may be performed by controllably positioning the radiation member within the radiation passageway beneath the expandable member and stent either before, during, or after the stent is implanted at the treatment site.

Another mode of the invention is a temporarily implantable brachytherapy device assembly having a radiation member with a radiation source engaged to the distal end of a delivery device, and also having a centering device with a centering member on its distal end portion and a centering lumen extending between a proximal port located proximally of the centering member and a distal location distally of the centering member. The centering device includes an outer tube, an inner tube that forms the centering lumen and that extends within the outer tube and distally therefrom, and a plurality of longitudinal splines that form the centering member. Each longitudinal spline has a proximal end secured to the outer tube and a distal end which is secured to the distal end portion of the inner tube extending distally from the outer tube. Each spline also extends along the longitudinal axis against the centering device when in the radially collapsed position and is adjustable to deflect radially outwardly from the centering device in the radially expanded position by adjusting either the outer tube distally relative to the inner tube or the inner tube proximally relative to the outer tube. According to one aspect of this mode, the distal end portion of the outer tube is secured to the distal end portion of the inner tube, and adjacent longitudinal cuts along the distal end portion of the outer tube form the splines. This centering device also allows perfusion of blood, or other bodily fluids, during the radiotherapeutic procedure.

Another mode of the present invention is a tissue radiation device assembly which includes a storage assembly for housing a radiation member that is adapted to removably engage a delivery member. The storage assembly according to this mode includes a housing with a storage chamber and also includes a radiation shield with an adjustable window adapted to engage the housing. The adjustable window is adjustable when engaged to the housing between an open position and a closed position relative to the storage chamber. In the open position, the storage chamber communicates externally of the housing through the adjustable window and the storage assembly is adapted to receive a radiation member within the storage chamber and also to have a radiation member removed from the storage chamber. In the closed position, the storage chamber is substantially radioactively isolated within the housing and the storage assembly is further adapted to store a radiation member within the storage chamber in substantial radioactive isolation.

In one aspect of this mode, the housing further includes a body with first and second ends on either side of the storage chamber. The storage chamber communicates through a first body port located along the first end of the body. Further to this aspect, a cover is rotatably engaged to the body's first end and includes a cover passageway extending between first and second cover ports. The cover is adjustable on the body between a first cover position to a second cover position. In the first cover position, the cover passageway communicates with the storage chamber such that the delivery member may be introduced into or removed from the storage chamber through the cover passageway and first body port. In the second cover position, the cover passageway is isolated from the storage chamber and the first body port is substantially closed and radioactively sealed by the cover.

In another aspect of this mode, a second window is coupled to the storage chamber at a location along the housing that is substantially opposite the first window. The second window is adjustable between a second open position and a second closed position relative to the storage chamber. In the second open position the storage chamber communicates externally of the housing through the second window. In the second closed position the storage chamber is substantially radioactively isolated within the housing at the second window. In one variation of this dual-window aspect, the second window is adjustable between the second open and closed positions when engaged to the housing. In a further dual-window variation, proximal and distal covers may be rotatably coupled to a body that forms the housing and are rotatable to adjust the first and second windows between their respective open and closed positions as previously described for the single window aspect.

In still a further dual-window variation of the storage assembly, a body coupler is engaged to the second window and is adapted to couple to a proximal coupler of a delivery member such that in the second open position the storage chamber communicates with a delivery lumen within the delivery member. According to this variation, a first delivery member is advanced through the first window in the open position and engages the radiation member within the storage chamber. With the second window then adjusted to the second open position, the first delivery member and engaged radiation member may then be advanced distally from the storage chamber through the second window and into the delivery lumen of a delivery member engaged to the body coupler.

Another mode of the invention is a tissue radiation device assembly with a storage assembly for storing a radiation member and also with a monitor coupled to the storage assembly to monitor a value of a predetermined parameter of the radiation member.

In one aspect of this mode, the predetermined parameter provides an indicia of the use of the radiation member, and according to one particular variation provides an indicia of the number of times the radiation member has been removed from the storage chamber. In another particular variation, the monitor is adapted to monitor the level of radioactivity of the radioactive source.

In a further aspect of this source monitoring mode, an indicator is coupled to the monitor and is adapted to indicate the value of the predetermined parameter. According to still a further variation, a processor is coupled to the monitor and in order to process the value of the predetermined parameter and to produce an output signal based upon the value. The indicator according to this further variation is also coupled to the processor and is adapted to receive the output signal from the processor and to indicate a result based upon the output signal. The indicator according to this aspect may be a visual display screen or a printer. In again a further variation, a computer readable storage medium is coupled to the processor and is adapted to receive the output signal and to store a result based upon the output signal in computer readable form.

Another mode of the invention is a tissue radiation device assembly with a storage assembly that has a housing with a plurality of storage chambers for storing several radiation members. These chambers can store: different radiation sources; radiation sources of varying lengths to treat various lesion lengths; radiation sources of varying diameter to treat different lumen diameters; and/or radiation sources of varying activity The storage assembly includes a radiation shield with a plurality of adjustable windows. Each adjustable window is coupled to a storage chamber and is adjustable relative to that storage chamber from an open position and a closed position When one of the windows is adjusted to its open position, the respective storage chamber communicates externally of the housing through the adjustable window and that storage assembly is adapted to receive a radiation member into the storage chamber or to have a radiation member removed from the storage chamber through the adjustable window. However, when the window is adjusted to its respectively closed position, the storage chamber is substantially radioactively isolated by the radiation shield.

In one aspect of this mode, the storage assembly includes a body with an adjustable cover. The body has first and second ends and contains the storage chambers between the first and second ends. Each storage chamber communicates externally of the body through a first body port located along the first end of the body. The cover rotatably engages the body's first end and includes a cover passageway extending between first and second cover ports. The cover is adjustable when engaged to the body such that the cover passageway is aligned with the first body port of any predetermined one of the storage chambers, such that the aligned storage chamber communicates exteriorly of the body through the cover passageway, or is aligned with none of the storage chambers, such that each storage chamber is substantially closed and radioactively isolated by the cover. According to this assembly, by aligning the cover passageway with a predetermined storage chamber a delivery member may be introduced into the predetermined storage chamber through the cover passageway and the first body port of the predetermined storage chamber to thereby engage a source coupler of a radiation member housed within the predetermined storage chamber and remove the radiation member from the housing.

In a further variation of this storage assembly mode, a second window is coupled to each storage chamber and opposite the respective first window also coupled to the storage chamber. Each second window is also adjustable between a second open position, wherein the respectively coupled storage chamber is adapted to communicate externally of the housing through the second window, and a second closed position, wherein the respective storage chamber is substantially radioactively isolated within the housing at least at the second window. By adjusting the first window of a particular storage chamber to its respective first open position, a delivery member may be advanced into the storage chamber through the first window and thereby couple to a source coupler on a radiation member housed within the storage chamber. By further adjusting the second window, also coupled to that storage chamber, to the second open position, the delivery member and radiation member may be advanced from the storage chamber and through the second window to thereby remove the radiation member from the storage assembly.

In one more detailed embodiment of this variation, the housing further includes at least one housing coupler that is adapted to couple to the second window of each of the storage chambers The housing coupler is also adapted to engage a second delivery member with a delivery lumen such that the delivery lumen is in communication with a storage chamber when the housing coupler is coupled to the second window of the storage chamber and when the second window is in the second open position.

The invention also includes methods for providing local tissue brachytherapy treatment to a region of tissue along a body space wall of a body space in a patient.

According to one method mode, a radiation source is engaged to a first delivery member and the radiation source is shielded from emitting radiation energy radially into body tissue proximally of the radiotherapy site during delivery to that site. Once delivered to the desired region of tissue, however, the radiation source is unshielded and centered within the body space and delivers a therapeutic dose of radiation to the region of tissue. After irradiating the tissue as just described, the radiation source is then removed from the body while again shielding the source from irradiating other regions of tissue.

A further method mode includes storing a radiation member with a radioactive source in substantial radioactive isolation within a storage chamber of a storage assembly. This method further includes adjusting a window engaged to the housing to an open position to thereby allow the storage chamber to communicate externally of the housing, engaging the radiation member with a delivery member inserted into the storage chamber through the open window, and removing the radiation member from the housing with the first delivery member so that it may be used for local tissue brachytherapy.

Still a further method mode of the invention includes removing a radiation source from a radiation shielded storage assembly so that it may be used as a local tissue brachytherapy procedure. After use, the radiation source is then replaced within and radioactively isolated within a storage chamber within the storage assembly where a predetermined parameter providing indicia of the use of the radiation source is monitored.

Yet another method mode of the invention includes coupling a monitor to a storage assembly for monitoring predetermined parameters such as indicia of the use of the radiation source type of radioisotope contained within the radiation source. In another aspect, the level of radioactivity of the radiation source is monitored when stored within the storage chamber. In a further aspect, the number of times a radiation source is used is monitored. In still a further aspect, the time by which the radiation source is used when removed from the assembly is monitored. In yet a further aspect, the radiation storage chamber has visual and/or audible alarms which will indicate the status of the position of the radiation source in relation to the housing and its respective ports and their positions.

BRIEF DESCRIPTION OF THE DRAWINGS

FIG. 6A shows a cross-sectioned end view taken along line 6A–6A through the radiation member storage assembly shown in FIG. 5A, and further shows the window of the storage assembly adjusted to a closed position.

FIG. 6B shows a cross-sectioned end view taken along line 6B—6B through the radiation member storage assembly shown in FIG. 5C, and further shows the window of the storage assembly adjusted to an open position.

FIG. 7 shows an exploded cross-sectioned longitudinal view of a tissue radiation member within a delivery passageway of a delivery catheter assembly, and shows in shadow view one particular coupling assembly adapted to interlockingly engage a first delivery member with the radiation member.

FIG. 8 shows a similar exploded cross-sectioned longitudinal view of a tissue radiation member and delivery catheter assembly as shown in FIG. 7, and shows another particular coupling assembly for the first delivery member and radiation member.

FIG. 9 shows an exploded perspective view of one particular coupling of a cover to a housing body according to a tissue radiation member storage assembly of the present invention.

FIG. 10A shows an end perspective view from within the interior of the cap shown in FIG. 9.

FIG. 10B shows a side view taken along line 10B—10B through the cap shown in FIG. 10A.

FIG. 11A shows a perspective longitudinal side view of the housing body shown in FIG. 9

FIG. 11B shows a transverse cross-sectional view taken along line 11B through the body shown in FIG. 11A.

FIG. 14A shows a longitudinal perspective view of another particular centering device which is adapted for use according to the tissue brachytherapy device assembly of the present invention.

FIG. 14B shows a longitudinal cross-sectional view taken along line 14B—14B through the centering device shown in FIG. 14A.

FIG. 14C shows a transverse cross-sectional view taken along line 14C—14C through the centering device shown in FIG. 14A.

FIG. 14D shows a transverse cross-sectional view taken along line 14D—14D through the centering device shown in FIG. 14A.

FIGS. 16A–D show perspective views of various sequential modes according to a method of using a tissue ablation device assembly of the present invention in combination with an endolumenal stent assembly along a stenosed region of a vessel lumen.

FIGS. 17A–D show perspective views of various sequential modes according to another method of using the tissue radiation device assembly according to the present invention in combination with either balloon angioplasty or endolumenal stenting.

DETAILED DESCRIPTION OF THE INVENTION

Figure 1:
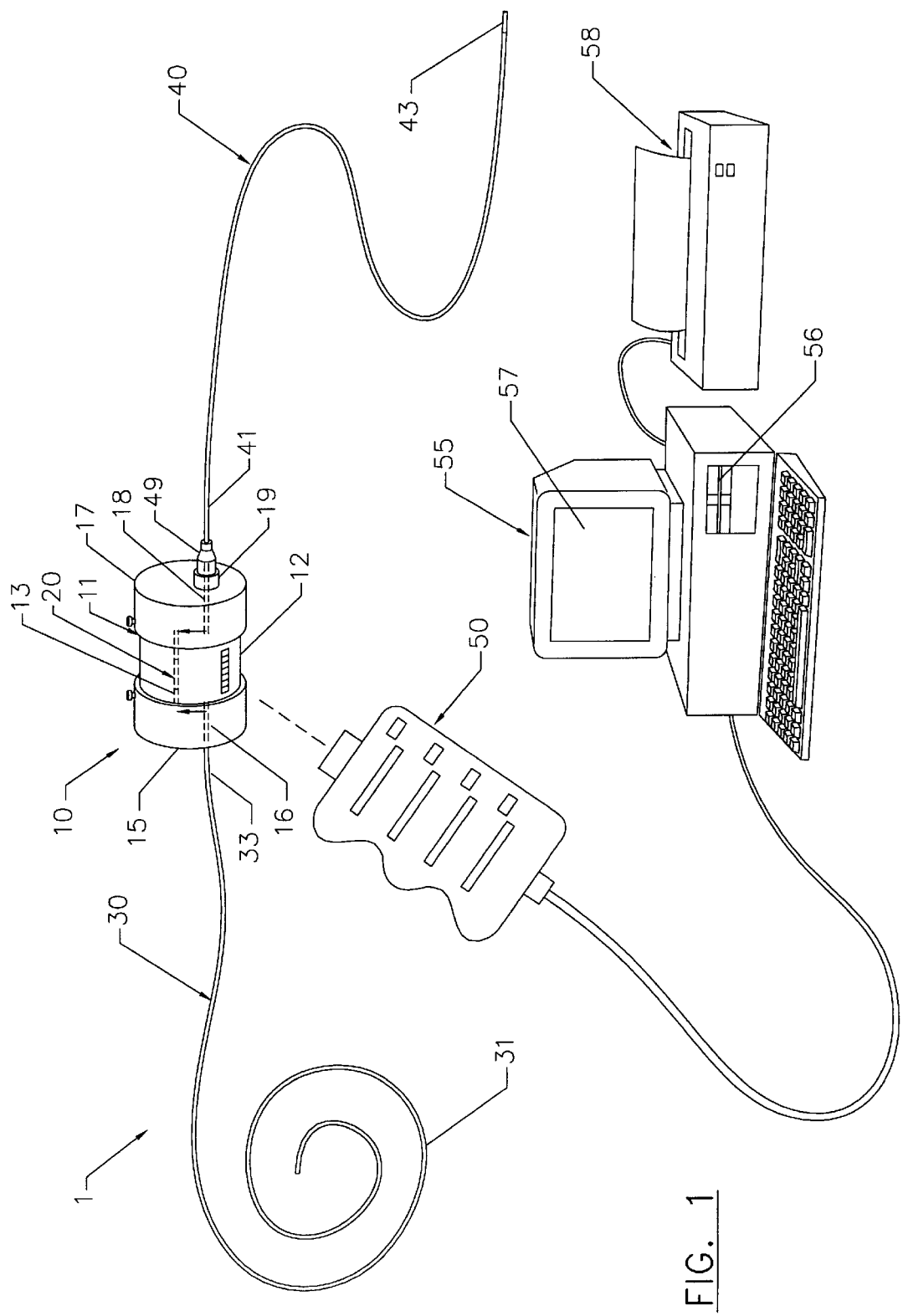
FIG. 1 shows a perspective view of a tissue brachytherapy device assembly according to the present invention.

FIG. 1 shows an overview of one tissue brachytherapy device assembly (1) according to the present invention and includes a storage assembly (10), a radiation member (20), a first delivery member (30), a second delivery member (40), and a monitor (50).

Storage assembly (10) is shown in FIG. 1 to include a housing (11) having a body (12) with a storage chamber (13) that houses radiation member (20) which is shown schematically in FIG. 1 and provided in more detail below. Housing (11) further includes a proximal cap (15) and a distal cap (17) which are each rotatably engaged with body (12) Body (12) and both proximal and distal caps (15,17) are constructed of material which is substantially radiopaque, such as for example but not limited to any one of tantalum, gold, tungsten, lead or lead-loaded borosilicate materials, and further including combinations, alloys or blends thereof. Therefore, in the specific embodiment shown, housing (11) also forms a radiation shield which is adapted to substantially radioactively isolate storage chamber (13) and to substantially prevent radiation member (20) from emitting radiation from storage chamber (13) and externally of storage assembly (10).

Housing (11) is shown in FIG. 1 to include proximal and distal passageways (16,18) extending through proximal and distal caps (15,17), respectively, and which are adapted to be selectively coupled to storage chamber (13). More specifically, according to the rotatable engagement of the caps with body (12) as just described, the respective passageways may be selectively aligned with the proximal and distal ends, also respectively, of storage chamber (13). According to this configuration, first and second windows are created at each of the proximal and distal ends of storage chamber (13), respectively, which are each adjustable between respectively open and closed positions relative to the storage chamber. Each window is shown in its respective closed position in FIG. 1, wherein both proximal and distal passageways (16,18) are out of alignment with the storage chamber (13) to thereby create the radiation isolating shield around storage chamber as described above. By rotating either cap so that its respective passageway is brought into alignment with storage chamber (13), as shown by way of illustrative arrows in FIG. 1, the respective window may therefore be adjusted to its open position. In the open position, storage chamber (13) communicates externally of storage assembly (10) through the respectively open window and aligned passageway, as is shown for the purpose of further illustration by reference to FIGS. 6A–B and as is further discussed below.

First delivery member (30) as shown in FIG. 1 is a delivery wire with a proximal end portion 31 and distal end portion 33. Distal end portion (33) is adapted to be introduced within proximal passageway (16). With the first or proximal window in the open position, as characterized by aligning proximal passageway (16) with storage chamber (13), distal end portion (33) of first delivery member (30) may be further advanced within storage chamber (13) where it is adapted to engage radiation member (20), as described in more detail below.

Also shown in FIG. 1, distal cap (17) further includes a body coupler (19) that is coupled to distal passageway (18). Second delivery member (40) is also shown in FIG. 1 to include a proximal delivery coupler (49) that is adapted to engage body coupler (19). Therefore, by adjusting the second or distal window to its open position, which is characterized by aligning the distal passageway (18) with storage chamber (13), radiation member (20) may be removed from storage chamber (13) through distal passageway (18), body and proximal delivery couplers (19,49), and an internal delivery lumen (not shown) through second delivery member (40).

Second delivery member (40) is shown schematically in FIG. 1 to include a proximal end portion (41) and a distal end portion (43). The internal delivery lumen (not shown) extends between a proximal delivery port at proximal delivery coupler (49) and a distal location along distal end portion (43). In one construction for second delivery member which is believed to be highly beneficial, proximal end portion (41) is made of a substantially radiopaque material and distal end portion (43) is made of a substantially radioluscent material According to this construction, distal end portion (43) may be placed at the desired in vivo location within a body space for tissue brachytherapy, and radiation member (20) may be delivered to that location through proximal end portion (41) without radially emitting radiation into proximal tissues which are not the intended site for brachytherapy, therefore preventing unwanted irradiation of healthy, normal tissue. In more particular constructions which are believed to be suitable according to this criteria, the proximal end portion may be made of polymers loaded with gold, tantalum, tungsten, barium sulfate particulates, a sheathing of any of these materials, or blends or combinations thereof, and distal end portion may be made of standard PTA catheter materials or low atomic number materials. For example, if preferred, a beryllium window may be used. In one more specific embodiment, the proximal end portion is made of tantalum material and the distal end portion is made of a polymeric and/or beryllium material.

It is to be further appreciated by view of FIG. 1 and by reference to the description above that radiation member (20) is delivered to the in vivo site through second delivery member (40), as just described, by means of first delivery member (30). This may be accomplished according to many different modes of using the beneficial features of the invention shown in FIG. 1. One specific mode is herein provided however for the purpose of further illustration. According to this specific mode of using the assembly shown in FIG. 1, proximal passageway (16) is aligned with storage chamber (13) while distal passageway (18) is left out of alignment with storage chamber (13), thereby opening the first proximal window at the proximal cap and maintaining the second distal window relative to the storage chamber (13) at the distal cap (17). First delivery member (30) is then advanced within the storage chamber (13) through the first, proximal window, forcing radiation member (20) distally within storage chamber (13) until a force may be exerted with first delivery member (30) onto radiation member (20) to allow interlocking engagement of the two members. With the proximal delivery coupler (49) of second delivery member (40) engaged to body coupler (19), distal cap (17) is then adjusted to align distal passageway (18) with storage chamber (13), thereby adjusting the second, distal window to its respective open position relative to storage chamber (13). First delivery member (30) may then be advanced distally to force radiation member (20) out of storage chamber (13) and into second delivery member (40).

It is to be further appreciated that distal end portion (43) of second delivery member (40) will be positioned at the desired brachytherapy location before engaging radiation member (20) and first delivery member (30) within its internal delivery lumen. Moreover, the distal location which the internal delivery lumen (not shown) terminates in second delivery member (40) may be a closed terminus or may be open, such as through a distal port (not shown) at the tip of second delivery member (40) although a closed terminus is preferred. In the variation where the distal location is a closed terminus, radiation member (20) may be completely isolated from intimate contact with body tissues, such as blood, and may therefore be recoverable post-procedure and reused in subsequent procedures. In this embodiment, however, second delivery member (40) may require further adaptation for positioning at the desired brachytherapy site, such as including a separate guidewire lumen adapted to track over a guidewire, or adapting second delivery member (40) to be controllable and steerable, such as having a shapeable/deflectable and torqueable tip, or adapting second delivery member (40) to slideably engage within another delivery lumen of yet a third delivery device positioned within the desired site. On the other hand, where the distal location of the internal delivery lumen is open at a distal port, the second delivery member (40) may be trackable over a guidewire engaged within the internal delivery lumen, and the guidewire may be simply removed after positioning, and replaced with the radiation member (20) and first delivery member (30). However, the "blood isolation" and therefore radiation member re-use benefits of the first, closed terminus variation are lost in a trade-off with the multi-functional aspects of the "open port" second variation, and therefore the radiation member may not be reuseable in this mode for the second delivery member.

Monitor (50) as shown in FIG. 1 is a bar-code reader and is adapted to read a bar-coded indicia provided on body (12), as also shown in FIG. 1. Monitor (50) is further shown interfaced with a computer (55), such as one having a computer readable and storable medium, such as a floppy disk drive (56), and a central processing unit (CPU) (not shown). Computer (55) is further shown interfaced with two displays for user interface: a visual monitor screen (57) and a hard-copy printer (58). While the particular assembly of components shown in FIG. 1 in relation to monitor (50) is believed to be highly beneficial, other variations are also contemplated which allow a user to monitor particular predetermined parameters of the stored radiation member prior to and/or after in vivo use.

For example, according to the bar-code variation shown, information about the radiation member that may be provided on the bar-code coupled to the housing body (12) may include any one or all of the predetermined parameters: half-Life of the radiation member; current activity; dose; dwell time (for prescribed treatment plan); radiation source serial number/lot number; report on actual treatment plan; etc. Upon reading this information with monitor (50), computer (55) may further process data that is pertinent to use of the radiation member in a particular procedure. For example, based upon monitored information of isotope activation date, prescribed dose, and the half-life of the source, the computer processor may calculate the decay rate, determine the real-time level of radioactivity of the radiation member, and further determine the dwell time necessary for a particular brachytherapy treatment in a patient (other patient-specific parameters may also be required to be entered, such as for example lumen-size of the intended brachytherapy site, which directly relates to distance away from the positioned source material, which directly relates to amount of radiation received at the lumen wall).

While the monitor according to the present invention is shown and described by reference to FIG. 1 in relation to a specific bar-code embodiment, other variations are also contemplated which may be suitably adapted to couple to storage assembly (10) such that a predetermined parameter of the radiation member stored therein may be monitored. For example, in another monitor variation not shown, a radiation monitor such as a Geiger counter may be coupled directly to the storage chamber of the storage assembly such that the actual level of radiation emitting from the radiation member stored therein may be directly monitored real-time, either before a brachytherapy procedure, after the procedure, or both. For the purpose of further illustration, a still further monitor variation also not shown includes a counter which provides indicia of the number of times a radiation member is used, such as for example by registering each time a window is adjusted to an open position which allows for the radiation member stored within the storage chamber to be engaged with a delivery member and removed for use.

Figure 2:
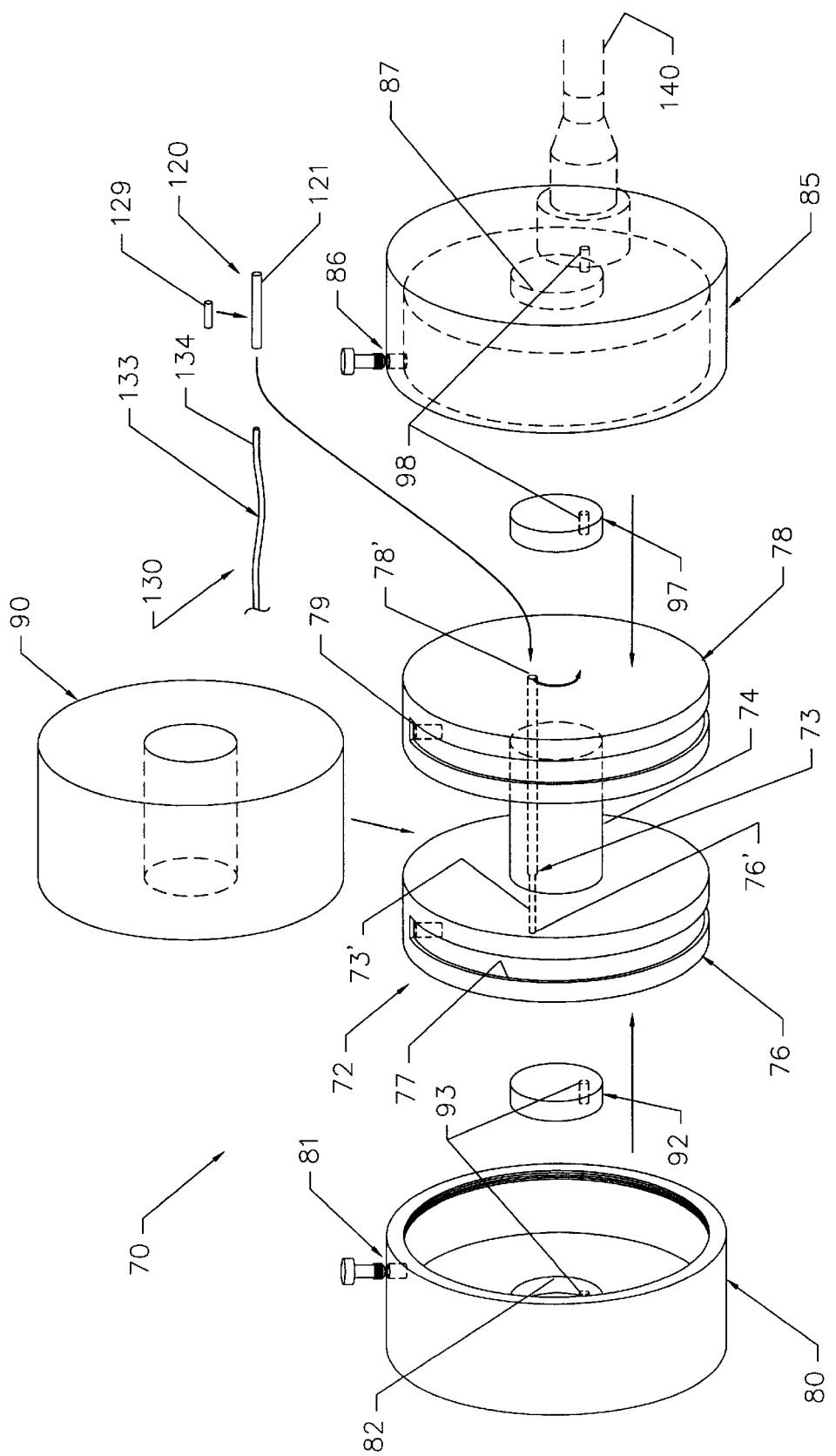
FIG. 2 shows an exploded view of various interactive features of the tissue brachytherapy device assembly shown in FIG. 1.
Figure 4A:
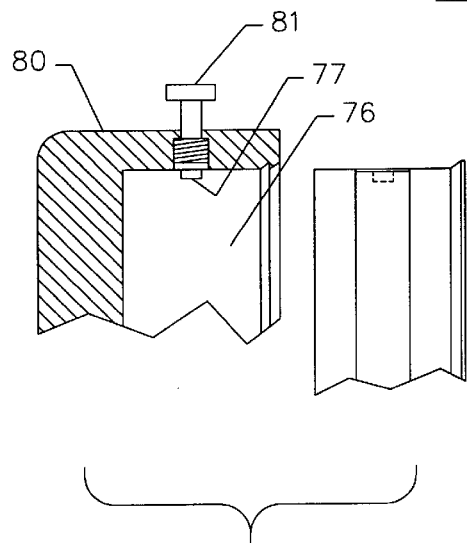
FIG. 4A shows an exploded cross-sectional side view of a particular housing and cover adapted to rotatably engage the housing in order to form a radiation shield with an adjustable window according to the storage assembly shown in FIG. 3.
Figure 4B:
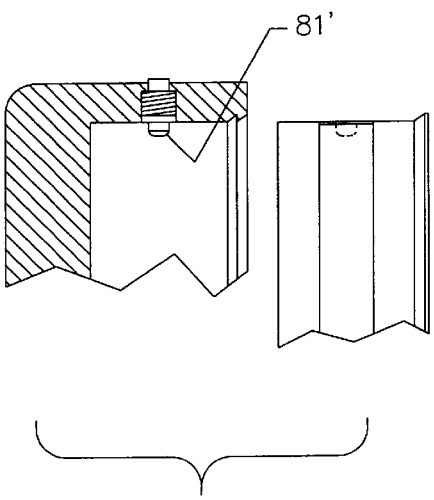
FIG. 4B shows an exploded cross-sectional side view of another particular housing and cover adapted to rotatably engage the housing in order to form a radiation shield within an adjustable window according to the storage assembly shown in FIG. 3.

One particular more detailed embodiment of a storage assembly which is believed to be suitable for use in a tissue radiotherapy device assembly such as that shown in FIG. 1 is shown in detail in FIG. 2. In more detail, FIG. 2 shows storage assembly (70) to include a body (72) with a central bore member (74) extending between proximal and distal coupling disks (76,78). Storage chamber (73) is shown in FIG. 2 as an elongate passageway that extends between a proximal port (76') on the proximal face of proximal coupling disk (76) and a distal port (78') on the distal face of distal coupling disk (78), and further includes a proximal narrow section (73') adjacent proximal port (76'). Proximal and distal circumferential grooves (77,79) are further provided along the outer circumferential surfaces of proximal and distal coupling disks (76,78), respectively. These circumferential grooves (77,79) are adapted to slideably receive detents from proximal and distal caps (80,85), also shown in FIG. 2. These detents are shown in the particular embodiment of FIG. 2 as adjustable screws (81,86) and are adjustable from a first position, wherein the respective cups (80, 85) are adapted to slideably engage and fit over the respective coupling disk, to a second position, wherein the screw is adjusted radially inward into the respectively coupled circumferential groove, as shown in one particular variation in FIG. 4A. In a still further variation shown in FIG. 4B, a rounded detent (81') may replace the screw detent variation, and may be coupled to a spring in a cam-follower type arrangement wherein the rounded detent (81') is adapted to ramp up a lip on the respective coupling disk and then spring back downward into the respective groove. Moreover, as further shown in FIG. 2, the circumferential grooves (77, 79) traverse only a portion of the outer circumferential surface of the respective coupling disks (76, 78). This allows for limited range of motion of the coupled caps between respective open and closed positions, as is also shown for the purpose of further illustration in FIGS. 6A–B.

Figure 3:
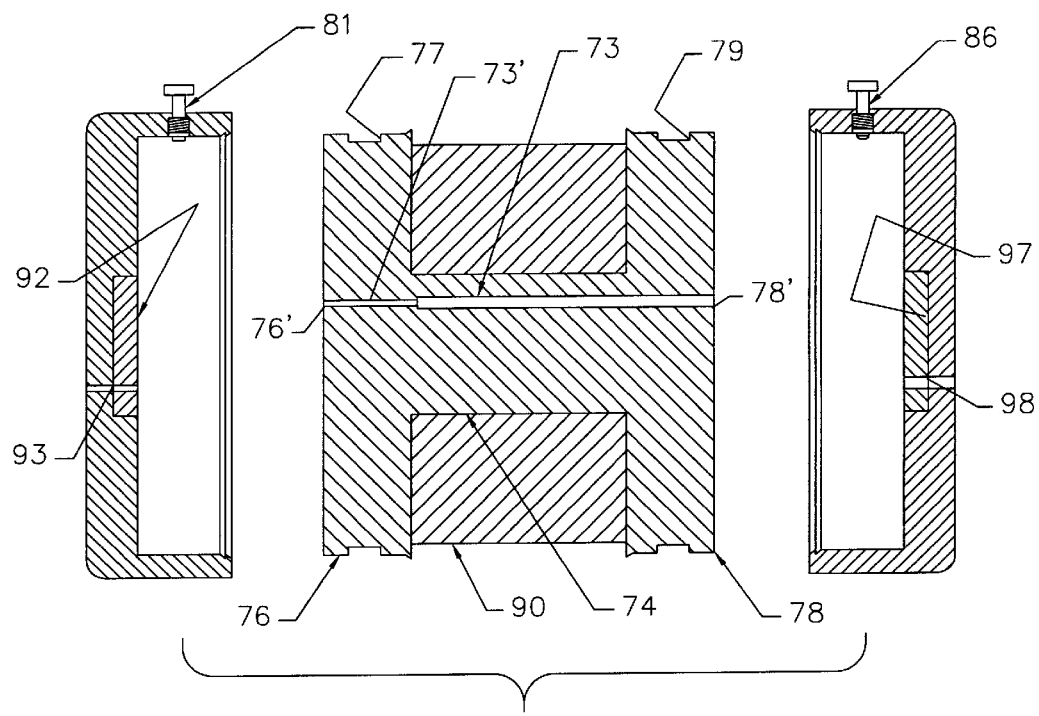
FIG. 3 shows a cross-sectional side view of a storage assembly adapted for use according to the tissue brachytherapy device assembly shown in FIGS. 1 and 20

According to the FIG. 2 embodiment storage assembly (70) further includes a radiation shield member (90) which is adapted to substantially radioactively isolate the storage chamber (73) within the assembly and which includes various components that are made of substantially radiopaque material, such as one or more of the materials previously described above. One such component shown in FIG. 2 is the cylindrical, radial shield member (90) which is adapted to surround central bore member (74) in order to provide a radial radiation shield relative to the storage chamber according to the overall assembly. Additional such shielding components which are shown in FIG. 2 include proximal and distal axial shields (92,97) which are shielded disks that are adapted to fit within recesses (82,87) provided by proximal and distal caps (80,85), respectively, and are further adapted to substantially cover the ends of central bore member (74). These axial shields (92,97), when coupled to caps (80,85), proximal and distal passageways (93,98), and, when coupled to body (72), form first, proximal and second, distal windows, also respectively, relative to storage chamber (73). Therefore, in the respective closed positions, the axial shields (92,97) are adapted to substantially radioactively isolate storage chamber (73) from axial radioactive emissions at its proximal and distal ends, respectively. The total radiation shield of storage assembly (70) is thereby formed by the combination of radial shield member (90) and proximal and distal axial shields (92,97) when these components are coupled to body (72) and proximal and distal caps (80,85), respectively. This interplay between components of storage assembly (70) shown in FIG. 2 is further shown in cross-section in FIG. 3 for the purpose of further illustration.

Figure 5A:
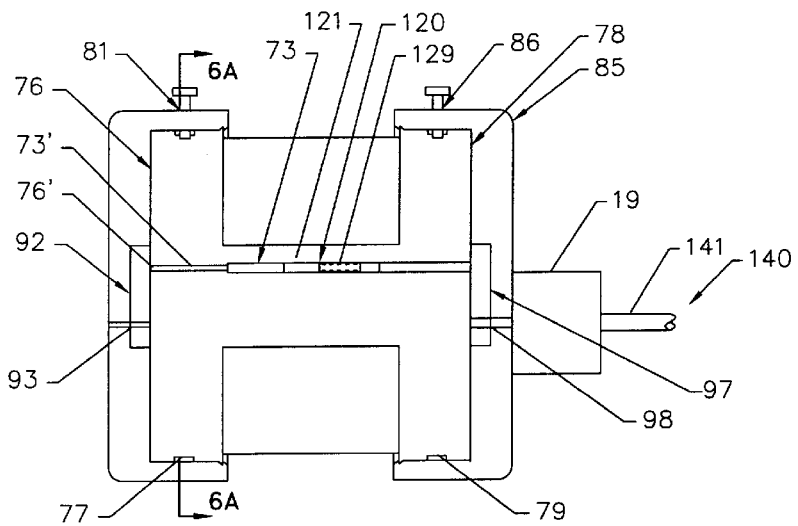
FIG. 5A shows a plan view of a radiation member storage assembly according to the present invention, and shows the interior components of the storage assembly, including a tissue radiation member housed within a storage chamber within a body of the storage assembly's housing, during one particular mode of use.
Figure 5B:
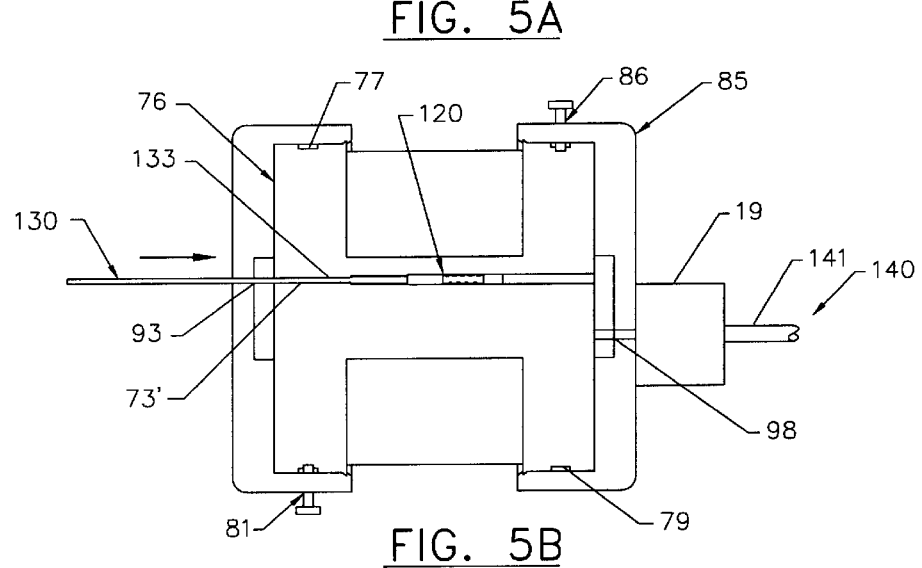
FIG. 5B shows a plan view of the radiation member storage assembly shown in FIG. 5B, although showing another particular mode of use wherein a first delivery member is shown advanced within the storage chamber through a window adjusted to an open position in order to couple to the radiation member.
Figure 5C:
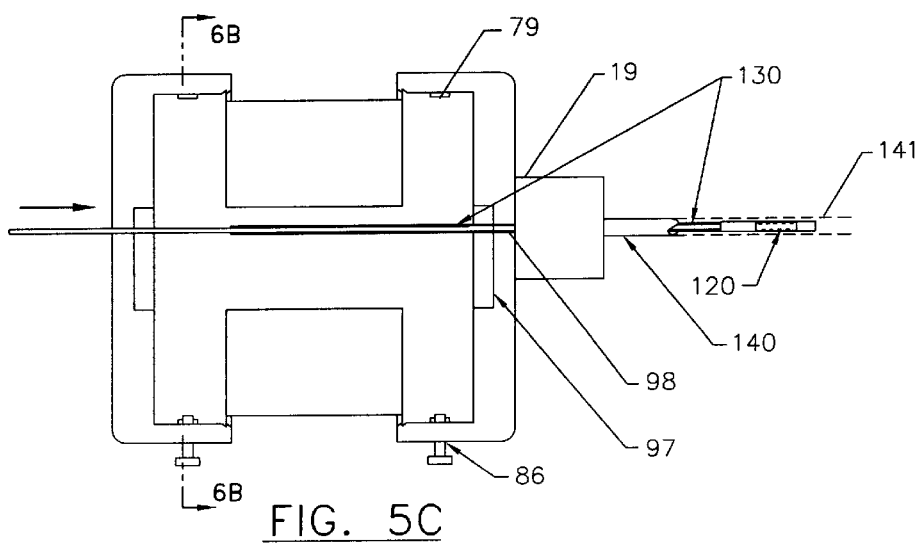
FIG. 5C shows a plan view of the radiation member storage assembly shown in FIGS. 5A–B, although showing another particular mode of use wherein the first delivery member and engaged radiation member are advanced from the storage chamber through a second window adjusted to a second open position and, shown in shadow view, into a delivery passageway of a delivery catheter assembly which is coupled to the second window

FIG. 2 further shows a particular radiation member (120) and first delivery member (130), which particular embodiments and are adapted for use with storage assembly (70). More particularly, radiation member (120) is adapted to be housed within storage chamber (73) and includes a source housing (121) and a radiation source (129), shown in exploded view, which includes a radioisotope. Particular radioisotopes which are believed to be suitable for use in provided localized, in vivo brachytherapy of tissue according to the present invention include, without limitation: thulium-170, phosphorus-32, rhenium-186, rhenium-188, cobalt-60, cesium-137, iridium-192, iodine-125, palladium-103, tantalum-73, tungsten-74, or gold-198. Further to first delivery member (130), distal end portion (133) is shown in FIG. 2 to include a formed tip having a geometry adapted to provide a delivery coupler (134) which may be received within a source coupler that forms a bore (not shown) within a proximal portion of radiation member (120). According to this embodiment, radiation member (120) may be engaged to the distal end portion (133) of first delivery member (130) by forcing delivery coupler (134) into the source coupler (not shown) when the first, proximal window is in the open position and the seconds distal window is in the closed position, and further while the radiation member (120) abuts axial shield (97) in distal cap (85), as previously described by reference to FIG. 2 above and as also shown for further illustration in FIGS. 5A–C.

Proximal narrow section (73') of storage chamber (73) as shown in FIG. 2 directly relates to the particular embodiment also shown in FIG. 2 for providing interlocking engagement between the first delivery member (130) and radiation member (120). More specifically, proximal narrow section (73') is adapted to have an internal diameter which is smaller than the internal diameter of the rest of the storage chamber (73) and which is also smaller than the outer diameter of radiation member (120). According to this design, after in vivo radiotherapy of tissues with radiation member (120) within second delivery member (140), radiation member (120) may be withdrawn proximally from second delivery member (140) and back within the storage chamber (73) until radiation member (120) confronts proximal narrow section (73') and thereby engages and is held by proximal narrow section (73') causing the radiation member to disengage from the first delivery member.

It is to be further appreciated that the present invention contemplates various alternative modes for providing interlocking engagement between the respective couplers of the radiation member and the first delivery member. Furthermore, particular modes may provide for different techniques for achieving the desired engagement between the member couplers within the storage chamber of the storage assembly. Two particular alternative embodiments for coupling delivery and source couplers according to the present invention are further illustrated in according to FIGS. 7–8 below.

FIG. 7 shows distal end portion (163) of first delivery member (160), radiation member (150), and second delivery member (170). Radiation member (150) includes a source housing (151) having two adjacent chambers which form source chamber (157) and source coupler (152), which two chambers are separated by an intermediate plug (156). Source chamber (157) is enclosed between intermediate plug (156) and distal plug (158) and is adapted to house a radiation source (159). Radiation source (159) is preferably constructed of a radioactive source material, such as those materials previously described above, and is further formed into the radiation member according to the following methods: machining from raw stock, swaging, forming from a billet. Source housing (151) is preferably constructed of stainless steel hypotube, and plugs (156, 158) are welded to the source housing enclosing the radiation source therein. Plugs (156, 158) are preferably made from 316L stainless steel.

Further to the FIG. 7 embodiment, source coupler (152) includes an interior surface (153) which forms a bore (154). First delivery member (160) includes a distal end portion (163) having a delivery coupler (164) with a spring (165) that is radially compressible against an outward bias force. Spring (165) is further adapted to be received and radially compressed within bore (154) such that the outward bias force engages interior surface (153) to provide the interlocking engagement. The mode for interlocking engagement is achieved by pushing first delivery member (160) against radiation member (150) within the storage chamber of the storage assembly, as previously described above. Moreover, this mode for interlocking engagement is reversible and detachable also within the storage chamber, such as previously described by reference to FIG. 2. According to the particular detachment mode of operation of the FIG. 7 embodiment, and by reference to both FIGS. 2 and 7, first delivery member (160) is pulled proximally through the storage chamber (73) which effectively allows proximal narrow section (73') to engage radiation member (150) and force it off of first delivery member (160) where it is again deposited for storage within storage chamber (73).

FIG. 8 shows an alternative threaded mode of engagement between first delivery member (180) and radiation member (170). First delivery member (180) has a delivery coupler (184) which is threaded. Radiation member (170) is constructed similarly to that shown and described by reference to the like member in FIG. 7, except that interior surface (173) of source coupler (172) in the FIG. 8 embodiment is threaded to mate with the threaded surface of delivery coupler (184). According to this embodiment, and by reference to both FIGS. 2 and 8, first delivery member (180) may be torqued and screwed into or out from radiation member (170) within storage chamber (73) when first delivery member (180) is either forced distally against radiation member (170) within storage chamber (73), or pulled proximally to force radiation member (170) against proximal narrow section (73'), respectively.

Both FIGS. 7 and 8 further show radiation members and first delivery members in a combination assembly with second delivery member (190). Second delivery member (190) is further shown in these Figures to include a delivery passageway (195) which extends between a proximal port (not shown) along a proximal end portion of second delivery member (190) and a distal location or terminus (198) along distal end portion (193) of second delivery member (190) which is substantially closed. In one preferred mode of use, distal end portion (193) of second delivery member (190) is adapted to be positioned within the body space, with the distal terminus (198) positioned distally of the desired location, by manipulating at least a part of the proximal end portion externally of the body. The specific second delivery member embodiment shown in FIG. 7 and 8 includes different material construction for proximal and distal end portions (191,193), preferably including a substantially radiopaque material and a substantially radioluscent material, respectively, as discussed previously above. Still further to the material construction of the FIG. 8 embodiment, distal terminus (198) is formed by a plug (199) which may be constructed from gold, platinum, platinum-iridium, tungsten, tantalum, or stainless steel and bonded to second delivery member (190) by cyanoacrylate UV adhesives or other suitable adhesives or bonding methods.

Second delivery member (190) according to FIGS. 7 and 8 is further adapted to slideably receive the first delivery member and engaged radiation member within the delivery passageway (195) through the proximal delivery port such that the radiation member is located within the delivery passageway (195) proximally adjacent the distal terminus (198) and along the desired location for tissue brachytherapy. According to the particular mode of construction for second delivery member (190) just described, the radiation member is therefore adapted to be delivered to the desired location without irradiating tissue proximally of the desired location, which is shielded by the substantially radiopaque proximal end portion (191), and also without irradiating tissues distally from second delivery member (190), which is shielded by the substantially radiopaque distal terminus (198).

A further variation to the particular storage assembly embodiments previously described above is shown in FIGS. 9–11B, wherein the particular storage assembly (200) shown is adapted to provide for a controlled and limited number of uses for a radiation member stored within a storage chamber (213) of the storage assembly (200). More specifically, storage assembly (200) includes a housing (201) with a cap (220) having a plurality of passageways or apertures (225). Cap (220) is also rotatably engaged to the housing's body (210) such that a ratchet assembly is formed between a ratchet or arm (222) on an interior surface of cover (220) and a plurality of circumferentially spaced recesses (215) forming a pawl which circumscribes an outer surface of body (210). This "ratchet-and-pawl" assembly is adapted relative to the plurality of passageways (225) such that cap (220) may be adjusted only in one direction and only a limited number of times to stepwise align each of the plurality of passageways (225) with storage chamber (213), Accordingly, the window into storage chamber (213) through which a first delivery member may be advanced to engage and remove the stored radiation member may be opened and closed only a predetermined number of times. Preferably this arrangement is designed to provide an optimum, controlled number of uses and reuses of a particular radiation member, and the embodiment shown in FIGS. 9–11B includes seven apertures or passageways in cap (220) to therefore allow for a maximum of seven sequential uses of a radiation member stored within the storage chamber of the assembly.

The embodiments shown and described above by reference to the previous Figures include a second delivery member which is adapted to provide a delivery lumen through which a radiation member and engaged first delivery member may be advanced into the desired location of a body space for tissue radiotherapy. However, it is to be appreciated that these previous embodiments represent only one delivery catheter assembly mode for delivering the radiation locally to the tissue. The present invention further contemplates use of a third delivery member such as a centering device for use in delivering the radiation member substantially at the radial center of the desired location within the body space. Various particular embodiments which are illustrative of such centering devices according to the present invention are shown variously in FIGS. 12A–14D.

Figure 12A:
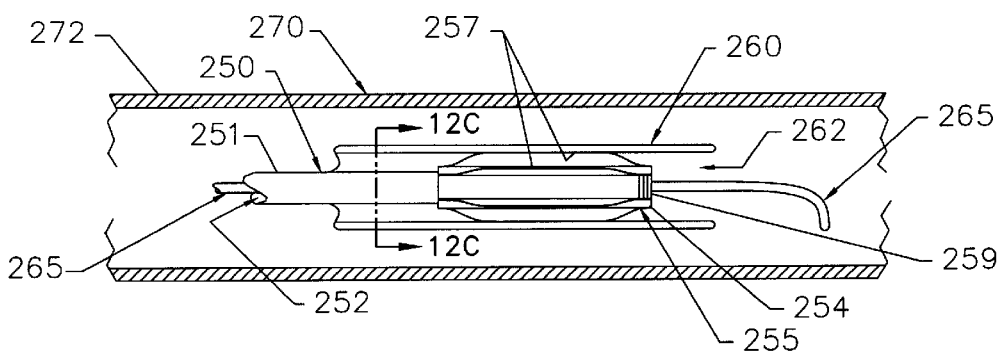
FIGS. 12A–B show perspective views of one particular centering device during two sequential modes of operation according to the tissue radiation device assembly of the present invention
Figure 12B:
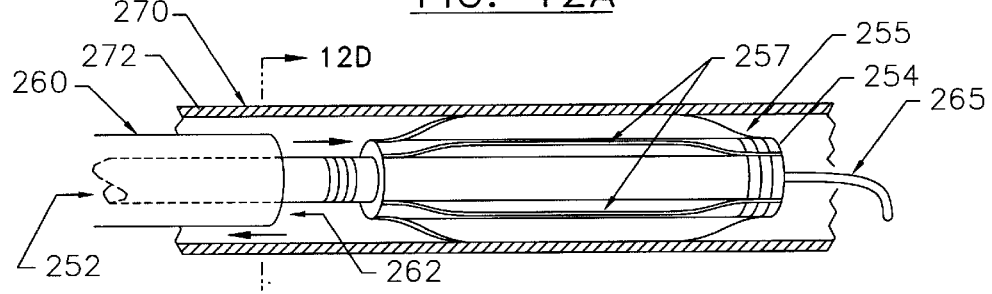
Figure 12C:
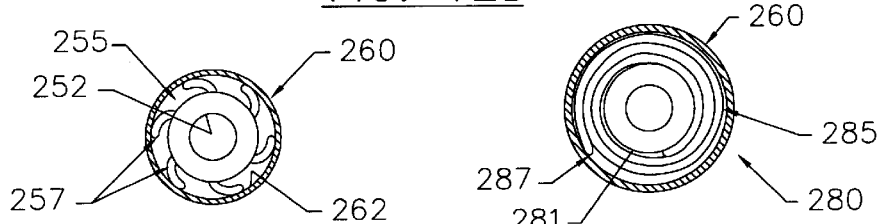
FIG. 12C shows a transverse cross-sectional view taken along line 12C—12C through the centering member and expansion member shown in FIG. 12A.
Figure 12D:
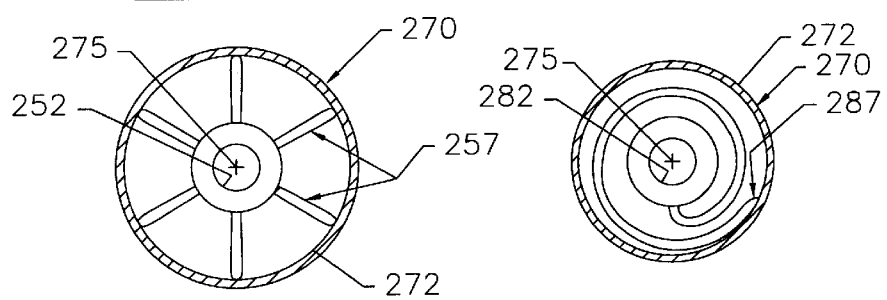
FIG. 12D shows a transverse cross-sectional view taken along line 12D—12D through the centering member shown in FIG. 12B.

More particularly to the centering device (250) shown in FIG. 12A, a centering member (255) is provided along a shaft (251) and in combination and within a lumen (262) of a slideable sheath (260). As shown by reference to both FIGS. 12A–B, and by further reference to FIGS. 12C–D, slideable sheath (260) is adjusted proximally relative to shaft (251) such that centering member (255) extends distally from the confines of the sheath and a plurality of longitudinal splines (257) located along centering member (255) are allowed to adjust from a first radially collapsed position (FIGS. 12A and 12C) to a second radially expanded position (FIGS. 12B and 12D). According to the radially expanded position, each of the longitudinal splines (257) is shown to engage the wall (272) of a lumenal vessel (270) to thereby act as a circumference of stand-offs that combine to center a centering passageway (252) along centering device (250) substantially at the radial center (275) of the vessel (270).

Further to FIGS. 12A–B, centering passageway (252) extends from a proximal port (not shown) along a proximal end portion of centering device (250) and to a distal port (259) along distal end portion (254) of centering device (250) distally of centering member (255). According to this embodiment, centering device (250) is therefore adapted to slideably engage a guidewire (265) into the centering passageway (252) and further to track over the guidewire (265) to the desired location of the body space for tissue radiotherapy. Once the centering device (250) is positioned over the guidewire at the desired location as shown, the guidewire (265) may then be removed and replaced with a radiation member engaged to further delivery members, such as for example to either one or both of the first and second delivery members as previously described above. In an alternative "guidewire tracking" variation not shown for the centering device, the centering passageway may be reserved for the sole use of delivering the radiation members whereas a separate passageway or lumen is further provided for tracking the centering device over a guidewire and to the desired location. According to this alternative, the centering passageway may be suitably closed and sealed from tissue contact such that a second delivery member is not necessary and the option for reuse of the radiation member is maintained.

In addition to the guidewire tracking modes just described for centering device (250) by reference to FIGS. 12A–B, other positioning modes for a centering device according to the present invention may also be suitable. For example, by further reference to the FIGS. 12A–D embodiments slideable sheath (260) may be first slideably engaged over the guidewire (265) and tracked to the desired location, after which the guidewire (265) may be removed proximally from the lumen (262) of the slideable sheath (260) and replaced with centering device (250) that then may advance distally through lumen (262) until centering member (255) is positioned at the desired location. Because the need for the centering device to track a guidewire is removed according to this mode, the centering passageway may thus be closed distally of the centering member in a further variation which allows for removal of the second delivery member from the overall delivery catheter assembly, replacing its features and function (as discussed according to the various embodiments above) with like features in the centering device itself, as previously described in the immediately preceding paragraph.

Further variations of the particular features of the centering member just shown and described by reference to FIGS. 12A–D may also be suitable according to the centering function also described.

Figure 12E:
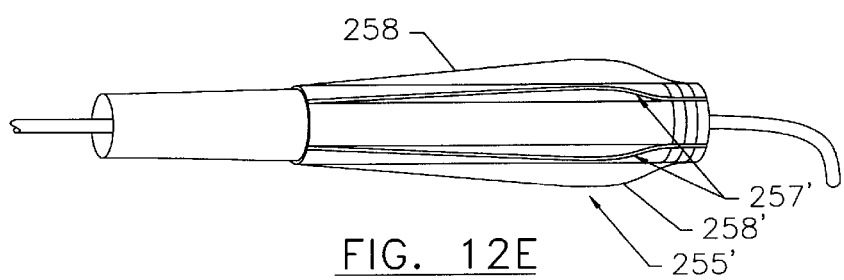
FIG. 12E shows a perspective view of one further embodiment of the centering member shown in various modes and views in FIGS. 12A–D.

For example, the centering member (255') shown in FIG. 12E includes similar longitudinal splines (257') as those provided by the FIGS. 12A–D embodiment, except that in this variation the splines (257') are tapered from a proximal reduced diameter section (258) to a distal larger diameter section (258'). This feature enhances advancement of the slideable sheath over the centering member for ease of retraction and removal of the device from the body.

Figure 13A:
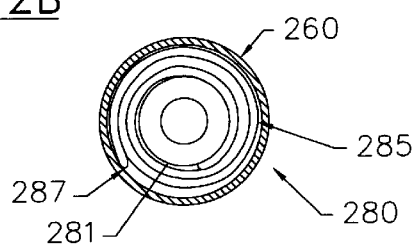
FIGS. 13A–B show transverse cross-sectional views of another centering member for use along a centering device according to the present invention, showing the centering member in radially collapsed and radially expanded positions, respectively.
Figure 13B:
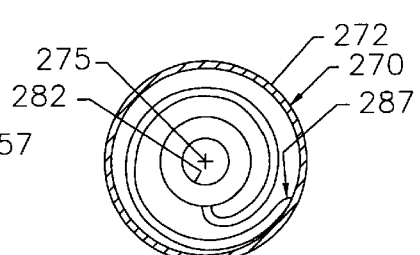

Another centering device variation is shown in FIGS. 13A–B and includes a centering member (285) with only one spline as a stand-off (287). More specifically, FIG. 13A shows stand-off (287) in a radially collapsed position which is wrapped circumferentially around a shaft (281) of centering device (280) when radially enclosed within an expansion member (260), which may be similar to the expansion member shown in FIGS. 12A–C. Once released from radial confinement by proximally withdrawing the slideable sheath, the stand-off (287) unwinds from its tight fold around shaft (281) and expands radially to a radially expanded position which engages the wall (272) of vessel (270) and positions centering passageway (282) substantially at the radial center (275) of the vessel (270).

Another centering device variation which is believed to be highly beneficial is shown in FIGS. 14A–D. By collective reference to these Figures, centering device (300) includes a centering member (330) with a plurality of longitudinal splines (335) that are formed between longitudinal cuts or grooves (314) that are cut into an outer tube (310) of the centering device (300). Outer tube (310) forms an outer tube lumen (312) through which an inner tube (320) is disposed, and outer tube (310) is secured to an outer surface of inner tube (320) distally of splines (335), such as for example by melt, solvent, or adhesive bonding these members together. During delivery to the desired location, the splines (335) are adapted to lay relatively flat relative to the longitudinal axis L of the assembly in a radially collapsed condition, as shown in FIGS. 14A–B and C, which condition characterizes the radially collapsed position of centering member (330). However, inner tube (320) is slideably engaged within outer tube lumen (312) such that by advancing outer tube (310) relative to inner tube (320), or withdrawing inner tube (320) relative to outer tube (310), the splines (335) are longitudinally compressed and collapse. This causes radial expansion of the splines (335) relative to the longitudinal axis L of the assembly, to a radially expanded condition that characterizes the radially expanded position for centering member (330), as shown in FIGS. 14A and D. Moreover, inner tube lumen (322) is further shown in FIGS. 14A–D to form a delivery passageway that is slideably engaged over a guidewire (340) which may be replaced with a radiation member engaged to further delivery components, such as one or both of the first and second delivery members as previously described.

It is of additional note that the centering design embodied on FIGS. 12A–E, 13A–B and 14A–D allow for perfusion of blood to minimize the incidence of ischemia encountered during such interventional procedures.

More complex assemblies and related methods are further contemplated which are believed to beneficially include the tissue radiation device assembly embodiments described above. More specifically, further assemblies for recanalizing stenosed regions of vessel lumens, such as blood vessels, and more particularly stenosed coronary arteries, may be beneficially combined with the embodiments described above in order to provide a mode for recanalizing a vessel in addition to preventing restenosis according to the tissue brachytherapy mode of the assembly.

Figure 15A:
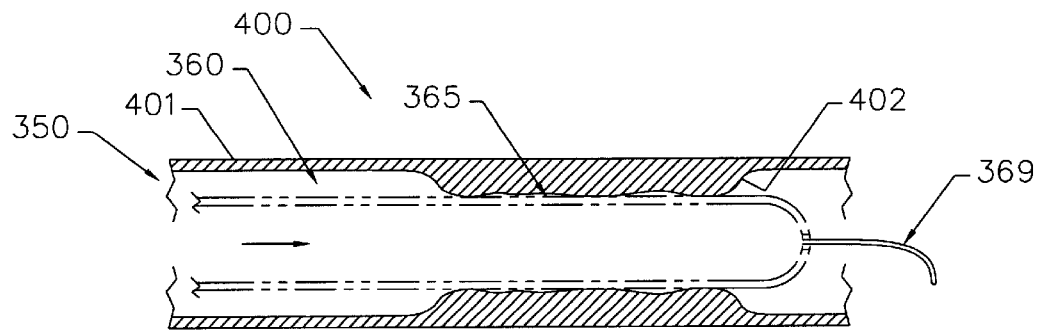
FIGS. 15A–D show perspective views of various sequential modes according to a method of using a tissue radiation device assembly of the present invention in combination with an angioplasty balloon catheter in a stenosed region of a vessel lumen.

One combination recanalization and tissue brachytherapy assembly (350) according to the present invention is shown in various modes of operation in FIGS. 15A–D and includes an angioplasty catheter (360) with a guidewire (369) in combination with an assembly of radiation member (370) and first and second delivery members (380,390), such as described in previous embodiments above. More specifically, FIG. 15A shows a schematic view of angioplasty catheter (360) as it is positioned over a guidewire (369) along a lumen (401) of a vessel (400) such that an angioplasty balloon (365) along angioplasty catheter (360) is located along a stenosed region (402) of vessel (400).

Figure 15B:
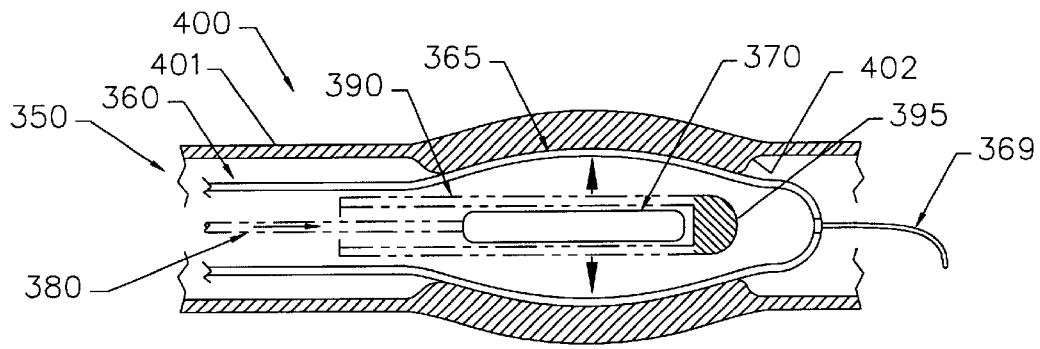
Figure 15C:
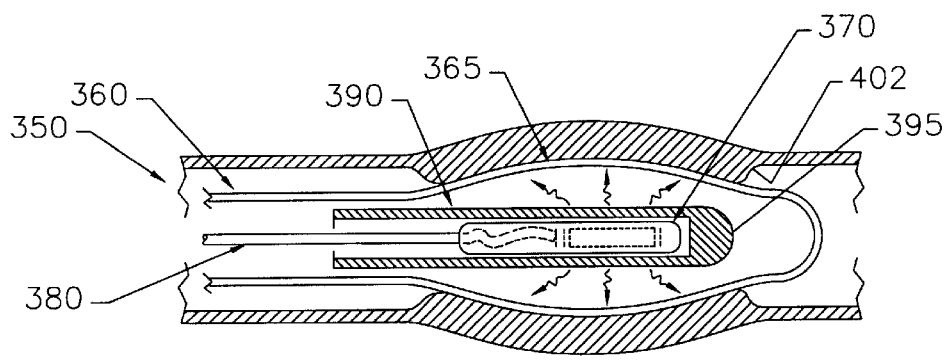

Balloon (365) is adapted to fluidly couple to a pressurizeable fluid source (not shown) for inflating and expanding balloon (365), as would be apparent to one of ordinary skill, and further as shown in FIG. 15B wherein the expanded balloon (365) dilates stenosed region (402) to thereby recanalize vessel (400). Guidewire (369) is removed from the balloon angioplasty catheter (360) and replaced with second delivery member (390) which is advanced within a passageway along angioplasty catheter (360) such that distal terminus (395) is located distally of balloon (365) as shown in FIG. 15C. First delivery member (380) is engaged to radiation member (370) and is advanced through second delivery member (390) until radiation member (370) is positioned within balloon (365), as previously described. Balloon (365) therefore serves as a centering device for positioning radiation member (370) substantially at the radial center of the stenosed region (402), also as previously described, such that radiation member (370) may locally irradiate the now dilated, stenosed region (402).

Figure 15D:
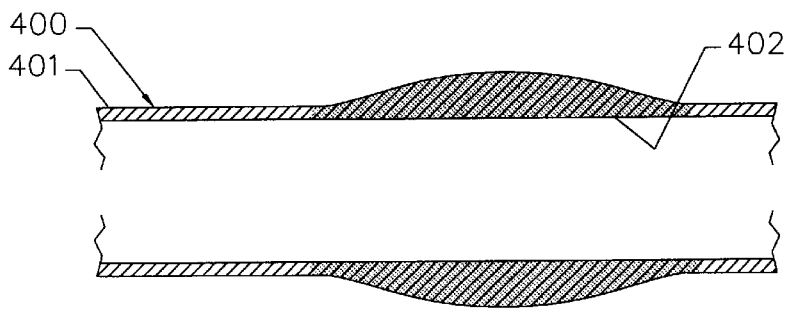

It is further contemplated that tissue brachytherapy according to this overall recanalization/brachytherapy device assembly may be performed either during or after angioplasty, and is shown for example during angioplasty in FIG. 15B, via shadowed representation of radiation member (370) and first and second delivery members (380,390) within balloon (365), and in FIG. 15C. Moreover, it is further contemplated that angioplasty may be first performed with angioplasty catheter (360), which is thereafter sequentially replaced with a separate centering device for use in a delivery catheter assembly for the radiation member (370). In any event, the beneficial result of the variations just described provide a dilated and locally irradiated stenosed region (402) of vessel (400), as shown in FIG. 15D.

Still a further recanalization/stent/radiotherapy assembly and method of use according to the present invention is shown in various modes in FIGS. 16A–D. As shown in FIGS. 16A–B, stenosed region (402) of vessel (400) is both dilated with an angioplasty balloon catheter (360) and stented with a stent (367). While the dilatation and stenting may be performed simultaneously with one angioplasty balloon engaged to a stent, it is further contemplated that these aspects of the overall assembly and use may be performed sequentially and with different angioplasty and stent delivery assemblies. In either case, FIG. 16C shows radiation member (370) and first and second delivery members (380,390) advanced within a centering device with a centering member engaged to the dilated and stented region (shown in FIG. 16C in one particular variation as the same angioplasty/stent delivery balloon), such as according to the modes of operating these tissue brachytherapy components as previously described by reference to the other embodiments. The beneficial result of the assembly and method just described is shown in FIG. 16D, and provides a dilated, stented, and locally irradiated stenosed region (402) of vessel (400).

It is further contemplated that the particular modes for operating the assemblies just described by reference to FIGS. 15A–16D may be further modified without departing from the scope of the present invention. For example, localized tissue radiation of the stenosed regions of vessel may be performed prior to recanalization or stenting methods described, as shown by way of further example in FIG. 17A.

FIG. 17A shows radiation member (370) engaged to first delivery member (380) and delivered into stenosed region (402) of vessel (400) through delivery passageway (392) of second delivery member (390) before stenosed region (402)

is recanalized or stented. Radiation member (370) is so delivered to the desired brachytherapy site generally according to methods previously described for operating an assembly of like components, and in the particular FIG. 17A embodiment an aperture or distal port (397) is formed through a stop (396). Further to this embodiment, port (397) allows second delivery member (390) to slideably engage and track over guidewire (369), shown in FIG. 17A in shadow, to the stenosed region (402). Guidewire (369) is then removed and replaced with first delivery member (380) and engaged radiation member (370). Moreover, port (397) has an inner diameter which is larger than the outer diameter of radiation member (370) such that stop (396) is adapted to prevent radiation member (370) from advancing distally out from second delivery member (390). As previously described, the guidewire tracking benefits of port (397) are balanced with the blood contact-reuse and radiation shielding benefits of providing a closed distal terminus to delivery passageway (392). In any event, subsequent modes according to the present embodiment are shown in FIG. 17B, wherein balloon angioplasty is performed post-brachytherapy, and FIG. 17C, wherein a stent is implanted into the stenosed region post-radiotherapy and either simultaneously or subsequent to angioplasty. The resultant recanalized and locally irradiated stenosed region (402) is shown in FIG. 17D, wherein stent (367) is shown in shadow as one variation adjunctive to dilating and locally irradiating the region.

Other embodiments not shown are further contemplated within the scope of the present invention. For example, other device and method modes adapted to recanalize a stenosed region of a vessel may be combined with the tissue radiation device assemblies shown and described In one particular example, atherectomy or other occlusion ablation device assemblies and methods may be perform adjunctively to tissue brachytherapy with the assemblies herein described without departing from the intended scope of the invention.

Moreover, additional modifications may be made to the particular embodiments which are shown in the Figures and herein described above without departing from the intended scope. For example, the storage assembly embodiments shown and described by reference to the Figures may be modified to include a separate shielding layer over the components of the housing, which components may therefore be constructed of materials which are not required to be substantially radiopaque. In another example, the particular embodiments described which provide adjacent substantially radiopaque and substantially radioluscent portions along either a second delivery member or a centering member are detailed variations of a broader aspect of the invention which provides a proximal radiation shield over the length of an overall radiation member delivery assembly. Other modifications are therefore further contemplated, such as in one specific aspect by providing a shielded sleeve over the second delivery member or centering device which is constructed of a substantially radiopaque material. Furthermore, the particular centering member or balloon angioplasty devices which are described above may be adapted to be over-the-wire, monorail, or fixed-wire in their construction and still be suitable for placement within a desired body space. Still further, while a novel feature of one device component may be shown and described above in combination with the novel features of other components, it is further contemplated that such novel features should be considered independently beneficial and may be suitably used in combination with more conventional components of an overall assembly.

Further, the aforedisclosed radiation therapy assembles and methods are applicable to the treatment of both vascular and non-vascular pathologies such as cancerous tumors.

Additional obvious variations and modifications to the embodiments herein described may be made by one of ordinary skill upon review of this disclosure and should be considered within the scope of the present invention.

What is claimed is:

1. A tissue radiation device assembly which is adapted to deliver radiation to a region of tissue at a desired location along a body space wall which defines at least a portion a body space in a patient, comprising:

a radiation member with a radiation source;

a first delivery member with a proximal end portion and a distal end portion which is adapted to engage the radiation member;

a second delivery member with a proximal end portion, a distal end portion, and a radiation passageway extending between a proximal port along the proximal end portion and a distal location along the distal end portion of the second delivery member wherein the radiation passageway is substantially closed in a fluid tight seal, the radiation passageway being adapted to slidably receive the first delivery member such that the radiation member engaged to the first delivery member may be positioned proximally of the distal location; and a third delivery member with a proximal end portion, a distal end portion, and a guidewire passageway extending between a distal guidewire port along the distal end portion of the third delivery member and a proximal guidewire port along the third delivery member proximally of the distal guidewire port, the guidewire passageway being adapted to slidably engage a guidewire through the proximal and distal guidewire ports and also to track over the guidewire into the body space such that the distal end portion of the third delivery member is positioned at the desired location, and the guidewire passageway also being adapted to slidably receive the second delivery member such that the distal end portion of the second delivery member may be positioned along the distal end portion of the third delivery member and within the body space at the desired location.

2. The tissue radiation device assembly of claim 1, the distal end portion of the third delivery member further comprising a centering member which is adapted to position the guidewire passageway substantially at the radial center of the body space at the desired location.

3. The tissue radiation device assembly of claim 2, wherein the third delivery member further comprises an elongate body with a longitudinal axis, an outer tube, and an inner tube, the outer tube having a proximal end portion, a distal end portion, and an outer tube lumen extending between the proximal and distal end portions of the outer tube, the inner tube having a proximal end portion slideably engaged within the outer tube lumen, a distal end portion extending distally from the outer tube lumen, and an inner tube lumen extending between a proximal centering port along the proximal end portion of the inner tube and the distal end portion of the inner tube, and the centering member being comprised of a plurality of longitudinal splines, each longitudinal spline having a proximal end secured to the outer tube and a distal end which is secured to the distal end portion of the inner tube, and each spline extending along the longitudinal axis in a radially collapsed position and being further adjustable to deflect radially outwardly in a radially expanded position by adjusting either the outer tube distally relative to the inner tube or the inner tube proximally relative to the outer tube;

wherein the inner tube lumen forms a centering passageway which is adapted to slidably receive the second delivery member, and wherein the centering member is adapted to position the centering passageway substantially at the radial center of the body space at the desired location by radially engaging the body space wall with the centering member in the radially expanded position.

4. The tissue radiation device assembly of claim 3, wherein the second delivery member further comprises a proximal shielded portion, which is adapted to substantially prevent radiation from transmitting radially from the radiation passageway, and a distal unshielded portion, which is adapted to substantially allow radiation to transmit radially from the radiation passageway.

5. The tissue radiation device assembly of claim 1, wherein the radiation member further comprises a source coupler and the first delivery member further comprises a delivery coupler, the delivery coupler being adapted to removably engage the source coupler.

6. The tissue radiation device assembly of claim 5, further comprising:

a storage assembly with a housing having a storage chamber and also with a radiation shield having a window which is engaged to the housing and is adjustable between an open position and a closed position relative to the storage chamber, wherein the open position the storage chamber is adapted to receive the radiation member within the storage chamber and to have the radiation member removably engaged within the storage chamber and removed from the storage chamber with the first delivery member, and wherein the closed position the storage chamber is adapted to store the radiation member within the storage chamber in substantial radioactive isolation at least relative to the window.

7. The tissue radiation device assembly of claim 6, further comprising:

a monitor adapted to couple with the storage assembly and which is further adapted to monitor a value of a predetermined parameter of the radiation member.

8. The tissue radiation device assembly of claim 1, the distal end portion of the second delivery member further comprising a stop positioned at the distal location within the radiation passageway and which is comprised of a radiopaque material.

9. A tissue radiation device assembly which is adapted to deliver radiation to a region of tissue at a desired location along a body space wall which defines at least a portion a body space in a patient, comprising:

a storage assembly with a housing having a plurality of storage chambers and also with a radiation shield having a plurality of adjustable windows, each adjustable window being coupled to a storage chamber and being adjustable between an open position and a closed position relative to the storage chamber, such that the storage chamber communicates externally of the housing when the window is adjusted to its open position wherein the storage assembly is adapted to receive a radiation member into the storage chamber or to have a radiation member removed from the storage chamber through the open window, and such that the storage chamber is substantially radioactively isolated by the radiation shield when the window is adjusted to the respective closed position.

10. The tissue radiation device assembly of claim 9, wherein each of the plurality of adjustable windows is a first window relative to one of the storage chambers, the open position for each of the plurality of adjustable windows is a first open position, and the closed position for each of the plurality of adjustable windows is a first closed position, and the radiation shield further comprising:

a plurality of second windows, each second window being coupled to a particular storage chamber opposite the first window also coupled to the particular storage chamber, and each second window also being adjustable between a second open position, wherein the particular storage chamber is adapted to communicate externally of the housing through the second window, and a second closed position, wherein the particular storage chamber is substantially radioactively isolated within the housing at least at the second window.

11. The tissue radiation device assembly of claim 10, further comprising:

a storage coupler coupled to one of the second windows and which is also adapted to couple to a proximal coupler of a delivery catheter assembly such that a delivery passageway within the delivery catheter assembly communicates with a storage chamber coupled to the second window.

12. The tissue radiation device assembly of claim 10, the housing further comprising a body comprised of radiation non-transmissive material and with proximal and distal ends, the storage chamber being located between the proximal and distal ends and communicating externally of the body through proximal and distal body ports located along the proximal and distal ends, respectively; and the storage assembly further comprising a proximal cover comprised of a radiation non-transmissive material and which is adapted to rotatably engage the proximal end of the body, and which further includes a proximal cover passageway extending between first and second proximal cover ports, the proximal cover when rotatably engaged to the proximal end of the body being rotatable such that each storage chamber may be selectively aligned with and communicate with the proximal cover passageway, which characterizes the first open position for the respectively aligned storage chamber, or may be substantially closed and radioactively isolated by the proximal cover, which characterizes the first closed position for the respective closed storage chamber; and a distal cover comprised of a radiation non-transmissive material and which is adapted to rotatably engage the distal end of the body, and which further includes a distal cover passageway extending between first and second distal cover ports, the distal cover when engaged to the distal end of the body being rotatable such that each storage chamber may be selectively aligned with and communicate with the distal cover passageway, which characterizes the second open position for the respectively aligned storage chamber, or may be closed by the distal cover, which characterizes the second closed position for the respective closed storage chamber.

13. The tissue radiation device assembly of claim 9, further comprising
a plurality of radiation members, each radiation member being housed within one of the plurality of storage chambers and including a radiation source and a source coupler which is adapted to engage a delivery coupler on a delivery member introduced into the respective storage chamber through the respective window in the open position.

14. The tissue radiation device assembly of claim 13, further comprising:
a first delivery member with a proximal end portion and a distal end portion with a delivery coupler, the distal end portion of the first delivery member being adapted to engage one of the plurality of storage chambers when the window coupled to the one of the plurality of storage chambers is in the open position and such that the delivery coupler is adapted to removably engage the source coupler of one of the plurality of radiation members housed within the one of the plurality of storage chambers, thereby removably engaging the radiation member with the first delivery member.

15. The tissue radiation device assembly of claim 14, further comprising:
a delivery catheter assembly with a proximal end portion and a distal end portion which is adapted to be positioned within the body space at the desired location by manipulating the proximal end portion of the delivery catheter assembly externally of the patient, and further comprising a delivery passageway extending between a proximal port along the proximal end portion of the delivery catheter assembly and a distal location along the distal end portion of the delivery catheter assembly,
the first delivery member being adapted to slideably engage the delivery passageway such that a radiation member engaged to the first delivery member may be positioned along the distal end portion of the delivery catheter assembly and at the desired location.

* * * * *